United States Patent
Kadowaki et al.

(10) Patent No.: US 6,976,382 B2
(45) Date of Patent: Dec. 20, 2005

(54) ABNORMALITY DIAGNOSING APPARATUS OF EXHAUST GAS SENSOR

(75) Inventors: Hisashi Kadowaki, Chita-gun (JP); Syujiro Morinaga, Takahama (JP); Yukihiro Yamashita, Takahama (JP); Hideyuki Maeji, Okazaki (JP)

(73) Assignee: DENSO Corporation, Kariya (JP)

( * ) Notice: Subject to any disclaimer, the term of this patent is extended or adjusted under 35 U.S.C. 154(b) by 0 days.

(21) Appl. No.: 10/368,403

(22) Filed: Feb. 20, 2003

(65) Prior Publication Data

US 2003/0154709 A1   Aug. 21, 2003

(30) Foreign Application Priority Data

| Feb. 20, 2002 | (JP) | 2002-043648 |
| Feb. 20, 2002 | (JP) | 2002-043649 |
| Mar. 6, 2002 | (JP) | 2002-060551 |
| Mar. 29, 2002 | (JP) | 2002-095422 |

(51) Int. Cl.[7] .................. G01N 7/00; G01N 21/00; G01N 33/496; G01L 3/26; F01N 7/00
(52) U.S. Cl. .................. 73/1.06; 73/23.31; 73/23.32; 73/119 R; 73/117.3; 60/272; 60/276; 60/277; 701/29; 701/99; 701/101; 340/438; 340/439
(58) Field of Search ................. 73/1.06, 118.1, 73/23.31, 23.32, 117.3, 117.2, 116, 119 R; 123/688; 60/272–280; 701/29, 99, 101; 340/438, 340/439

(56) References Cited

U.S. PATENT DOCUMENTS

| 5,444,977 | A | * | 8/1995 | Kawabata | 60/276 |
| 5,758,632 | A | | 6/1998 | Yamashita et al. | |
| 5,964,208 | A | | 10/1999 | Yamashita et al. | |
| 5,970,967 | A | * | 10/1999 | Uchikawa | 123/688 |
| 6,396,021 | B1 | * | 5/2002 | Sato et al. | 73/118.1 |
| 2002/0023430 | A1 | * | 2/2002 | Takaku et al. | 60/277 |

FOREIGN PATENT DOCUMENTS

| JP | 9-170966 | 6/1977 |
| JP | 88-285808 | 11/1996 |
| JP | 10-169501 | 6/1998 |

* cited by examiner

Primary Examiner—Daniel S. Larkin
Assistant Examiner—Tamiko Bellamy
(74) Attorney, Agent, or Firm—Nixon & Vanderhye P.C.

(57) ABSTRACT

At a time point at which an ignition switch is made OFF and an engine is stopped, an output of a downstream gas sensor is read, thereafter, at a time point at which a predetermined time period has elapsed from stopping the engine, the output of the downstream gas sensor changed by flowing the atmosphere back into an exhaust pipe is read. Thereafter, a change in the output of the downstream gas sensor until the predetermined time period has elapsed from stopping the engine is calculated, the change in the output is compared with an abnormality determinant and when the change in the output is smaller than the abnormality determinant, response of the downstream gas sensor is determined to be abnormal.

35 Claims, 19 Drawing Sheets

ABNORMALITY DIAGNOSING APPARATUS OF EXHAUST GAS SENSOR

CROSS REFERENCE TO RELATED APPLICATION

This application is based on and incorporates herein by reference Japanese Patent Applications No. 2002-43648 filed on Feb. 20, 2002, No. 2002-43649 filed on Feb. 20, 2002, No. 2002-60551 filed on Mar. 6, 2002 and No. 2002-95422 filed on Mar. 29, 2002.

FIELD OF THE INVENTION

The present invention relates to an abnormality diagnosing apparatus of an exhaust gas sensor for diagnosing presence or absence of an abnormality of the exhaust gas sensor based on an output of the exhaust gas sensor installed in the exhaust path of an internal combustion engine.

BACKGROUND OF THE INVENTION

In exhaust gas cleaning systems of a vehicle, exhaust gas sensors (air/fuel ratio sensors or oxygen sensors) for detecting an air/fuel ratio or rich/lean of exhaust gas are installed on an upstream side and a downstream side of a catalyst for cleaning the exhaust gas. The air/fuel ratio is feedback-controlled based on outputs of the exhaust gas sensors to thereby promote an exhaust gas cleaning efficiency of the catalyst.

In the exhaust gas cleaning systems, a deterioration in the exhaust gas sensors is diagnosed in order to prevent operation from being continued in a state in which accuracy of the air/fuel ratio control is lowered (state in which an exhaust gas cleaning rate is low) by deteriorating the exhaust gas sensors. According to the method of diagnosing the deterioration of the exhaust gas sensors, generally, presence or absence of the deterioration of the exhaust gas sensors is determined by whether a change of the outputs of the exhaust gas sensors follow a change in the air/fuel ratio with excellent response when the air/fuel ratio is changed.

However, the change of the outputs of the exhaust gas sensor installed on the downstream side of the catalyst is influenced by a cleaning function of the catalyst (storage effect) Therefore, a delay occurs until the change in the air/fuel ratio (target air/fuel ratio λTG) on the upstream side of the catalyst emerges as a change in the air/fuel ratio on the downstream side of the catalyst (output of exhaust gas sensor). The delay time period is changed by the cleaning function and a degree of deterioration of the catalyst at the time point. Therefore, when the deterioration of the exhaust gas sensor is diagnosed based on the change of the output of the exhaust gas sensor on the downstream side of the catalyst, the change of the output of the exhaust gas sensor on the downstream side of the catalyst is influenced to change by the cleaning function of the catalyst (storage effect) at the time point and presence or absence of the deterioration of the exhaust gas sensor on the downstream side of the catalyst cannot accurately be determined.

Hence, as shown by JP-A-9-170966, a time period during which an output of an oxygen sensor on a downstream side of a catalyst is changed from a rich side set value to a lean side set value at each cutting of fuel is measured as a response time period. Presence or absence of deterioration in the oxygen sensor on the downstream side of the catalyst is determined by whether the response time period is equal to or longer than a deterioration determinant (primary diagnosis). As a result, in the case in which the determination is determined to be present, when cutting off fuel is carried out continuously for a predetermined time period, at a time point at which an elapse time period after recovery from cutting off fuel reaches a set time period, a minimum response time period which has been measured until the time point is read from a memory to compare with the deterioration determinant and when the response time period is determined to be equal to or longer than the deterioration determinant again, the oxygen sensor on the downstream side of the catalyst is firmly diagnosed to be deteriorated.

According to the apparatus, when diagnosing the deterioration of the oxygen sensor on the downstream side of the catalyst, an influence of the storage effect of the catalyst is disregarded by cutting off fuel. That is, by utilizing a property that the response time period from starting to cut off fuel until the air/fuel ratio on the down stream side of the catalyst is changed to be lean since in cutting off fuel, a large amount of lean component ($O_2$ or the like) flows into the catalyst and an amount of adsorbing the lean component in the catalyst is rapidly brought into a saturated state, the deterioration of the oxygen sensor is diagnosed by measuring the response time period of the oxygen sensor on the downstream side of the catalyst in cutting off fuel.

However, actually, the response time period of the oxygen sensor on the downstream side of the catalyst is changed by the storage effect of the catalyst. That is, as shown in FIG. 5, when the air/fuel ratio on the upstream side of the catalyst is switched from rich to lean by cutting off fuel, in the midst of changing the air/fuel ratio on the downstream side of the catalyst (output of oxygen sensor) is being changed from rich to lean, the air/fuel ratio on the downstream side of the catalyst hardly changes temporarily by the storage effect of the catalyst. The more progressed is the degree of deterioration of the catalyst, the shorter a duration time period of the storage effect and the response time period of the oxygen sensor on the downstream side of the catalyst is shortened. Therefore, in diagnosing the deterioration of the oxygen sensor on the downstream side of the catalyst, the influence of the storage effect of the catalyst cannot be disregarded and presence or absence of the deterioration of the oxygen sensor on the downstream side of the catalyst cannot accurately be determined.

Further, when the air/fuel ratio is changed in operating an engine for diagnosing the abnormality of the exhaust gas sensor, adverse influence is effected on exhaust emission or drivability.

Further, when the abnormality diagnosis is carried out after waiting for a change in the air/fuel ratio under a predetermined condition by cutting off fuel, depending on a method of operating a vehicle or a road situation, chances of changing the air/fuel ratio under the predetermined condition are reduced and the frequency of carrying out the abnormality diagnosis is reduced and the abnormality of the exhaust gas sensor may not be detected at early time. Further, when the abnormality diagnosis is carried out by forcibly changing the air/fuel ratio on the upstream side of the catalyst (target air/fuel ratio) in operating the engine in order to ensure the frequency of carrying out the abnormality diagnosis, a running function or an exhaust cleaning function of the catalyst may be deteriorated.

SUMMARY OF THE INVENTION

It is a first object of the invention to carry out abnormality diagnosis of an exhaust gas sensor under a condition of excluding influence of a storage effect of a catalyst.

In order to achieve the first object, presence or absence of an abnormality of an exhaust gas sensor is diagnosed based on an output of the exhaust gas sensor after stopping an internal combustion engine. After stopping the internal combustion engine, exhaust gas is not exhausted from the internal combustion engine to an exhaust path but the atmospheric air flows back from an exhaust port of the exhaust path into the exhaust path. Therefore, in accordance with an elapse of a time period after stopping the internal combustion engine, an atmosphere at a periphery of the exhaust gas sensor becomes proximate to an atmospheric state. Therefore, in a process in which the atmosphere at the periphery of the exhaust gas sensor becomes proximate to the atmospheric state by flowing back the atmosphere into the exhaust path after stopping the internal combustion engine, by monitoring how the output of the exhaust gas sensor is changed, presence or absence of the abnormality of the exhaust gas sensor can be determined. Thereby, the abnormality of the exhaust gas sensor can be diagnosed after stopping the internal combustion engine and adverse influence is not applied to exhaust emission or drivability at all.

It is a second object of the invention to carry out abnormality diagnosis of an exhaust gas sensor on a downstream side of a catalyst and to promote accuracy of diagnosing abnormality of the exhaust gas sensor on the downstream side of the catalyst under a condition in which influence of a storage effect of the catalyst is reduced.

In order to achieve the second object, abnormality diagnosis of the downstream gas sensor is carried out based on an output of the downstream gas sensor in an operating region exceeding cleaning function of the catalyst. In the operating region exceeding the cleaning function of the catalyst, a storage amount (adsorption amount) of a lean component or a rich component in a catalyst is brought into a saturated state, exhaust gas passing through the catalyst without being cleaned thereby is increased. Therefore, a change in an air/fuel ratio on the upstream side of the catalyst emerges as a change in an air/fuel ratio on the downstream side of the catalyst with excellent response. Thereby, the abnormality diagnosis of the downstream gas sensor can be carried out based on the output of the downstream gas sensor under a condition in which the influence of the storage effect of the catalyst is reduced in comparison with that in a related art and presence or absence of the abnormality of the downstream gas sensor can accurately be determined.

Here, an operating region exceeding the cleaning function of the catalyst is an operating region in which a flow rate of rich/lean component in exhaust gas flowing to the catalyst exceeds a function of cleaning reaction (oxidation, reduction, adsorption) of the catalyst. The larger the flow rate of the exhaust gas, the larger the flow rate of the rich/lean component in the exhaust gas flowing into the catalyst. Further, the flow rate of the exhaust gas flowing to the catalyst can indirectly be detected from the intake air amount detected as an engine control parameter even when the flow rate is not directly detected.

It is a third object of the invention to accurately carry out abnormality diagnosis of an exhaust gas sensor on a downstream side of a catalyst without being influenced by the catalyst and ensure the frequency of carrying out the abnormality diagnosis without effecting adverse influence on a running function or an exhaust gas cleaning function of the catalyst.

In order to achieve the third object, abnormality diagnosis of a downstream gas sensor is carried out by introducing an abnormality diagnosing gas to an upstream side of the downstream gas sensor in an exhaust path on a downstream side of the catalyst.

When the abnormality diagnosing gas is introduced to the downstream side of the catalyst (upstream side of the downstream gas sensor) directly without passing the catalyst, an environment flowing at a periphery of the downstream gas sensor can be changed by the abnormality diagnosing gas without being influenced by the catalyst. Therefore, by monitoring whether the output of the downstream gas sensor is changed in correspondence with a change in the atmosphere flowing at the periphery of the downstream gas sensor by a state of introducing the abnormality diagnosing gas, abnormality diagnosis of the downstream gas sensor can be carried out without being influenced by the catalyst and presence or absence of abnormality of the downstream gas sensor can accurately be determined.

Further, abnormality diagnosis can be carried out by forcibly changing the state of introducing the abnormality diagnosing gas. Therefore, it is not necessary to carry out the abnormality diagnosis after awaiting for a change in the air/fuel ratio under a predetermined condition and the frequency of carrying out the abnormality diagnosis can be ensured without being influenced by a method of operating a vehicle or a road situation. Further, it is not necessary to forcibly change an air/fuel ratio on an upstream side of the catalyst (target air/fuel ratio) in diagnosing abnormality. Therefore, an air/fuel ratio feedback control can be continued even in executing abnormality diagnosis and adverse effect is not effected on running function or exhaust gas running function of the catalyst.

It is a fourth object of the invention to provide an abnormality diagnosing apparatus of an exhaust gas sensor capable of accurately detecting abnormality of the exhaust gas sensor per se on a downstream side of a catalyst without being influenced by a deterioration in the catalyst.

To achieve the fourth object, a correction amount for correcting an air/fuel ratio of an internal combustion engine is set and stored respectively for an operating condition of the internal combustion engine based on a detected value of the exhaust gas sensor on a downstream side of the catalyst of the internal combustion engine and abnormality of the exhaust gas sensor is diagnosed based on the stored correction amount of the respective operating condition. Therefore, abnormality of the exhaust gas sensor per se on the downstream side of the catalyst is accurately detected without being influenced by an ageing change of the catalyst.

BRIEF DESCRIPTION OF THE DRAWINGS

The above and other objects, features and advantages of the present invention will become more apparent from the following detailed description made with reference to the accompanying drawings. In the drawings.

DESCRIPTION OF THE PREFERRED EMBODIMENTS (First Embodiment)

Figure 1:
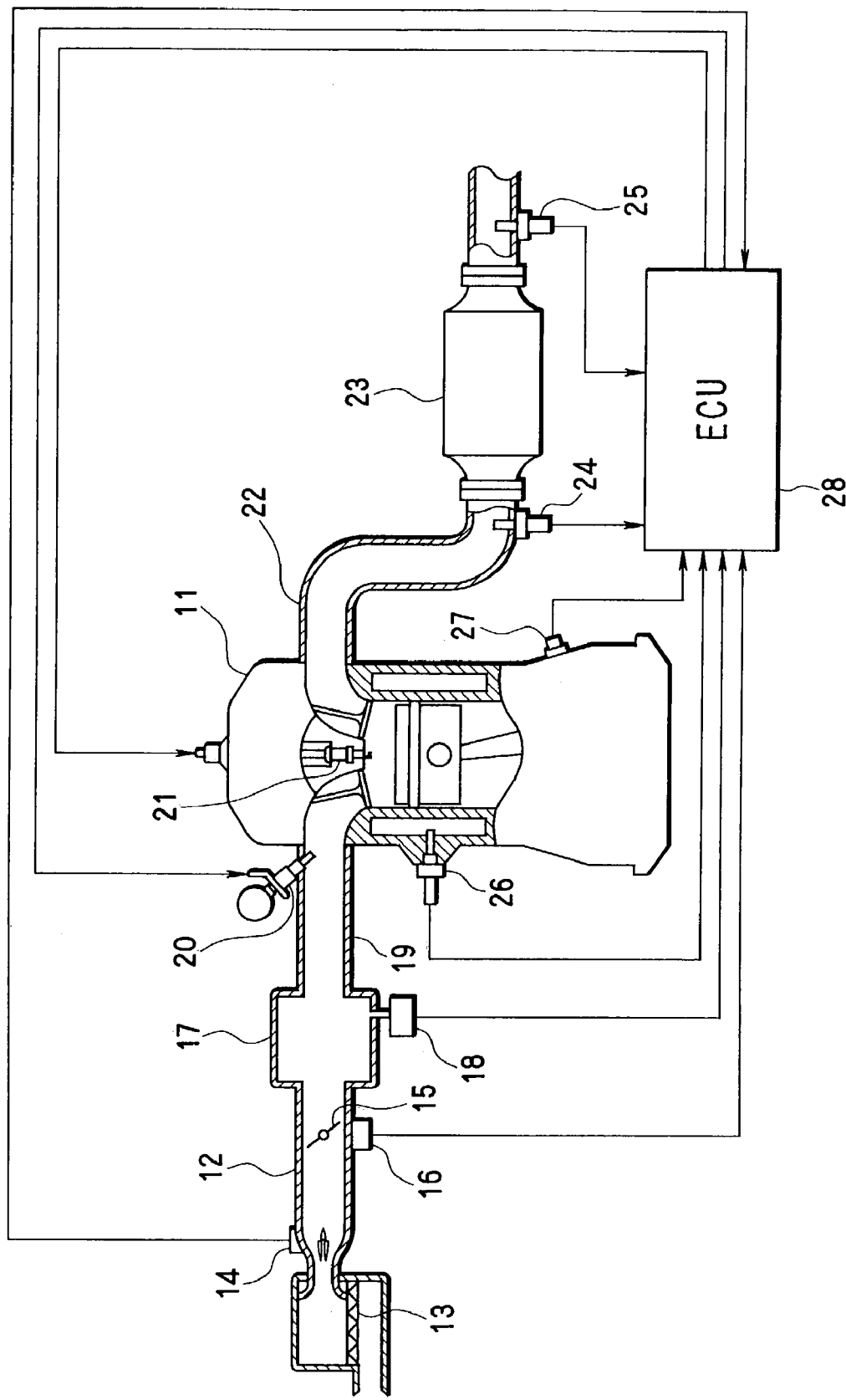
FIG. 1 is a schematic view of an engine control system according to a first embodiment of the present invention.

A first embodiment of the invention will be described in reference to FIG. 1 through FIG. 3. An air cleaner 13 is installed at the most upstream portion of an intake pipe 12 of an engine 11 which is an internal combustion engine and an air flow meter 14 for detecting an intake air amount is installed on the downstream side of the air cleaner 13. A throttle valve 15 and a throttle opening degree sensor 16 for detecting a throttle opening degree are installed on the downstream side of the air flow meter 14.

Further, a surge tank 17 is provided on the downstream side of the throttle valve 15 and the surge tank 17 is installed with an intake pipe pressure sensor 18 for detecting intake pipe pressure. Further, the surge tank 17 is installed with an intake manifold 19 for introducing air to each cylinder of the engine 11 and a fuel injection valve 20 for respectively injecting fuel is attached at a vicinity of an intake port of the intake manifold 19 of each cylinder. A cylinder head of the engine 11 is attached with an ignition plug 21 for each cylinder and mixture gas in the cylinder is ignited by spark discharge of each ignition plug 21.

Meanwhile, an exhaust pipe 22 (exhaust path) of the engine 11 is installed with a catalyst 23 of a three-way catalyst for cleaning CO, HC, NOx in exhaust gas and exhaust gas sensors 24 and 25 (air/fuel ratio sensor, oxygen sensor) for detecting an air/fuel ratio or lean/rich respectively are provided on the upstream side and the downstream side of the catalyst 23, respectively.

Further, a cylinder block of the engine 11 is attached with a cooling water temperature sensor 26 for detecting cooling water temperature and a crank angle sensor 27 for detecting engine rotational speed NE.

Outputs of the various sensors are inputted to an engine control circuit (ECU) 28. ECU 28 is mainly constructed with a microcomputer for controlling a fuel injection amount of the fuel injection valve 20 and an ignition time point of the ignition plug 21 in accordance with an engine operating state by executing various control programs stored in a ROM (storage medium).

Figure 2:
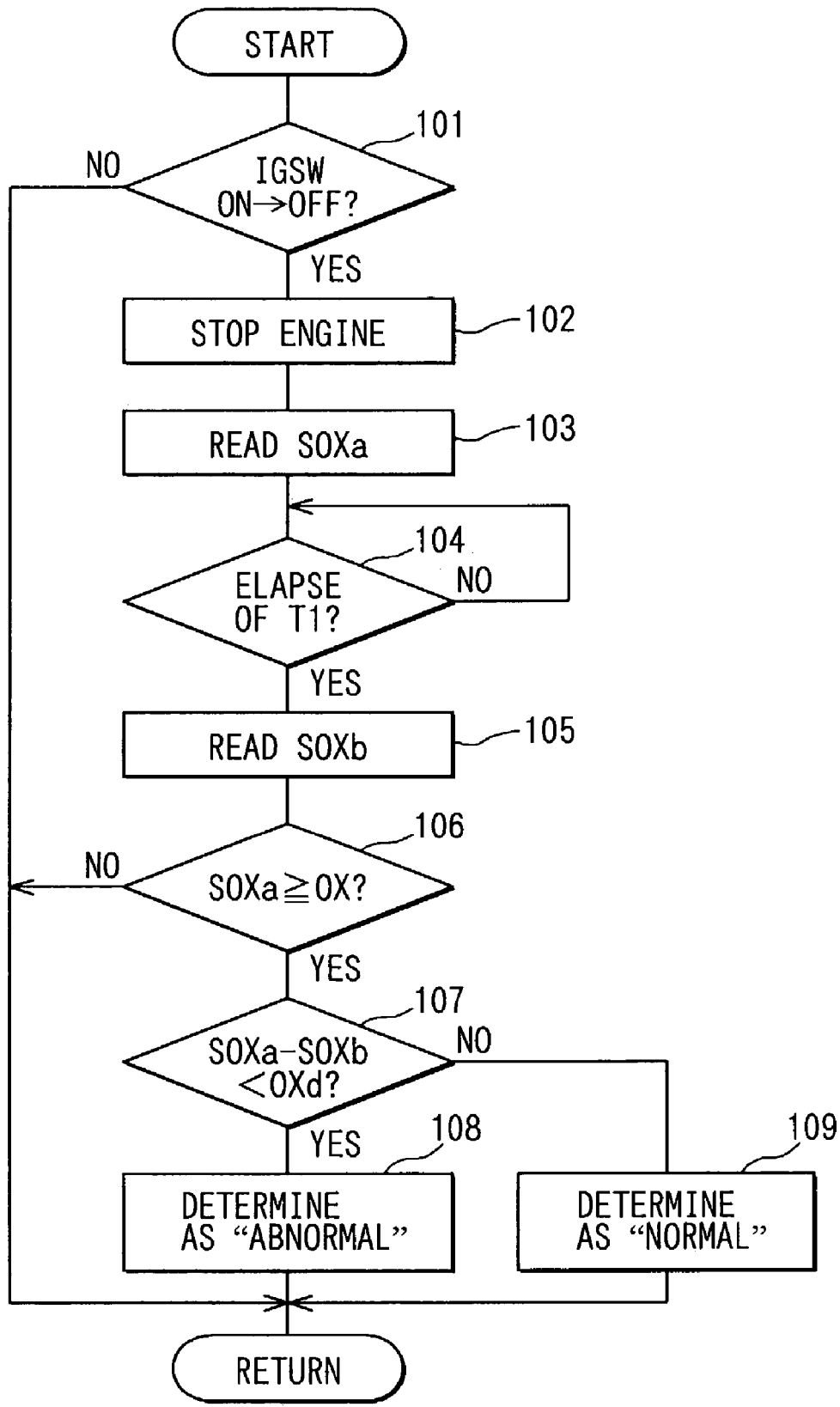
FIG. 2 is a flowchart showing a processing of an exhaust gas sensor abnormality diagnosing program according to the first embodiment.

Further, by executing an exhaust gas sensor abnormality diagnosis program shown in FIG. 2, based on the output of the exhaust gas sensor (downstream gas sensor) 25 on the downstream side of the catalyst 23 after stopping the engine, ECU 28 diagnoses presence or absence of abnormality of the downstream gas sensor 25 to thereby execute abnormality diagnosis of the downstream gas sensor 25 under a condition excluding influence of the storage effect of the catalyst 23 after stopping the engine 11.

The exhaust gas sensor abnormality diagnosis program is executed at a predetermined period in operating the engine and during a time period from stopping the engine 11 until abnormality diagnosis of the downstream gas sensor 25 has been finished. The program is executed at stopping the engine. Therefore, during the time period from stopping the engine until the abnormality diagnosis of the downstream gas sensor 25 has been finished, electric power is supplied to both of ECU 28 and the downstream gas sensor 25.

When the program is started, first, at step 101, it is determined whether an ignition switch (IGSW not illustrated) is switched from ON to OFF. When the ignition switch is not switched from ON to OFF, the program is finished without executing processing thereafter. Thereafter, when it is determined that the ignition switch is switched from ON to OFF, the processing proceeds to step 102, fuel injection and ignition are finished to thereby stop the engine 11. Thereafter, the processing proceeds to step 103 and reads an output SOXa (FIG. 3) of the downstream gas sensor 25 at stopping the engine.

Thereafter, the processing proceeds to step 104 and it is determined whether a predetermined time period T1 has elapsed from stopping the engine. As shown in FIG. 3, the predetermined time period T1 is set to a time period shorter to some degree than a time period required for reducing the output of the downstream gas sensor 25 which is normal to a vicinity of an atmospheric level. Further, at a time point t2 at which the predetermined time period T1 has elapsed from stopping the engine (time point t1), the processing proceeds to step 105 and reads the output SOXb (FIG. 3) of the downstream gas sensor 25 after the predetermined time period T1 has elapsed from stopping the engine.

Thereafter, the processing proceeds to step 106 and it is determined whether the output SOXa of the downstream gas sensor 25 at stopping the engine is equal to or larger than a predetermined value OX (for example, a value set to a lean side of a stoichiometric air/fuel ratio). When the output SOXa of the downstream gas sensor 25 at stopping the engine is smaller than the predetermined value OX, a change width until the output of the downstream gas sensor 25 is changed to the atmospheric level after stopping the engine is reduced. Therefore, the program is finished without executing abnormality diagnosis processing of steps 107 through 109 by determining that accuracy of diagnosing abnormality of the downstream gas sensor 25 may be deteriorated since a difference in change of sensor output between the normal exhaust gas sensor and the abnormal exhaust gas sensor is reduced. The processing at step 106 thus prohibits abnormality diagnosis.

Meanwhile, when it is determined that the output SOXa of the downstream gas sensor 25 at stopping the engine is equal to or larger than the predetermined value, the processing proceeds to step 107, calculates a difference between the output SOXa of the downstream gas sensor 25 at stopping the engine and an output SOXb of the downstream gas sensor 25 after the predetermined time period T1 has elapsed from stopping the engine, that is, an output change width (SOXa–SOXb) of the downstream gas sensor 25 until the predetermined time period T1 has elapsed from stopping the engine and determines whether the output change width (SOXa–SOXb) is smaller than an abnormality determinant OXd. The abnormality determinant OXd is set based on a characteristic of flowing atmosphere into the exhaust pipe 22 after stopping the engine estimated previously by experiment or simulation. In this case, a change (change speed, change width) until the output of the downstream gas sensor 25 has changed to the atmospheric level after stopping the engine is changed in accordance with a gas concentration at a periphery of the downstream gas sensor 25 at stopping the engine. Therefore, the abnormality determinant OXd is calculated by a map or an equation in accordance with the output SOXa of the downstream gas sensor 25 at stopping the engine.

At the step 107, when it is determined that the output change width (SOXa–SOXb) of the downstream gas sensor 25 until the predetermined time period T1 has elapsed from stopping the engine is smaller than the abnormality determinant OXd, the processing proceeds to step 108, and determines that response of the downstream gas sensor 25 is abnormal (deteriorated).

In contrast thereto, when it is determined at step 107 that the output change width (SOXa–SOXb) of the downstream gas sensor 25 until the predetermined time period T1 has elapsed from stopping the engine is equal to or larger than the abnormality determinant, the processing proceeds to step 109 and determines that the response of the downstream gas sensor 25 is normal (not deteriorated) and finishes the program.

After stopping the engine, the exhaust gas is not exhausted from the engine 11 to the exhaust pipe 22, the atmospheric air flows back into the exhaust pipe 22 from an exhaust port (not illustrated) of the exhaust pipe 22. Therefore, the atmosphere at a periphery of the downstream gas sensor 25 becomes proximate to the atmospheric state in accordance with elapse of time after stopping the engine. Further, the atmospheric air flowing back to the periphery of the downstream gas sensor 25 constituting the object of abnormality diagnosis, does not pass the catalyst 23. Therefore, the atmosphere at the periphery of the downstream gas sensor 25 becomes proximate to the atmospheric state without undergoing the influence of the storage effect of the catalyst 23 at all.

Figure 3:
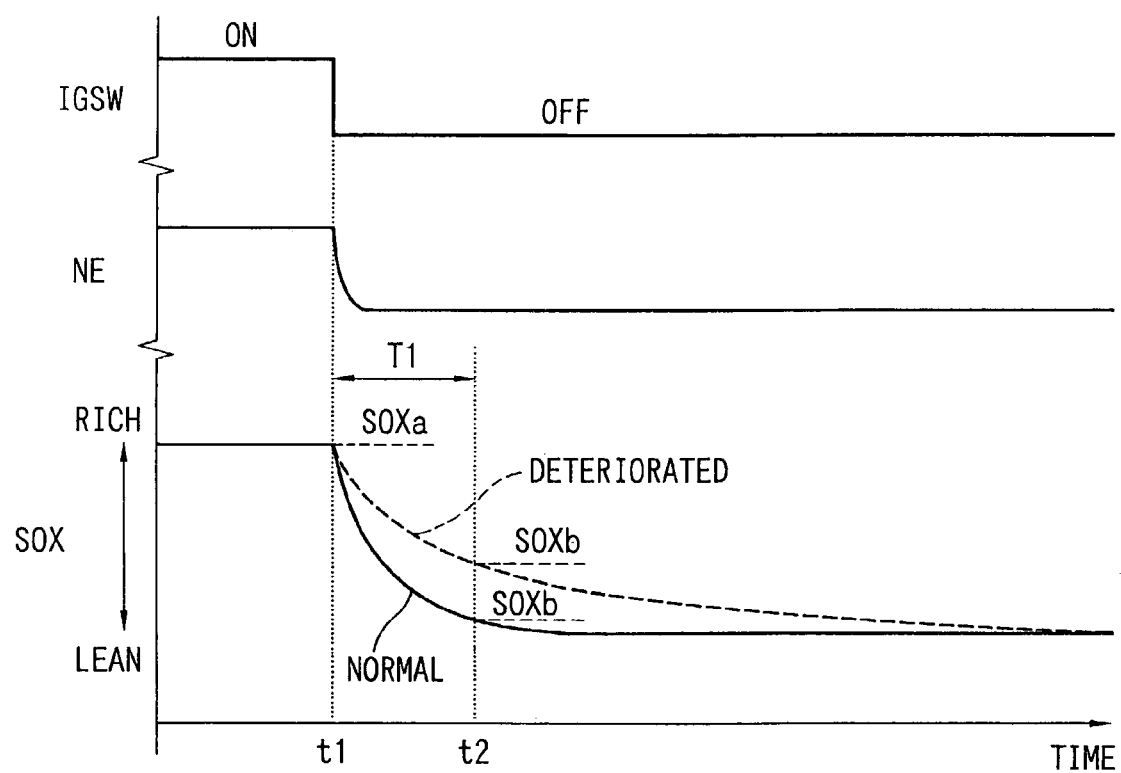
FIG. 3 is a time chart showing an example of carrying out the first embodiment.

According to the first embodiment, as shown in FIG. 3, at the time point t1 at which the ignition switch is made to OFF and the engine 11 is stopped, the output SOXa of the downstream gas sensor 25 is read, thereafter, at a time point T2 at which the predetermined time period T1 has elapsed from stopping the engine, the output SOXb of the downstream gas sensor 25 changed by flow back of the atmospheric air into the exhaust pipe 22 is read. Further, the output change width (SOXa–SOXb) of the downstream gas sensor 25 until the predetermined time period has elapsed from stopping the engine is calculated and the output change width (SOXa–SOXb) is compared with the abnormality determinant OXd to thereby diagnose presence or absence of abnormality of response of the downstream side of the exhaust gas sensor 25.

When the response of the downstream gas sensor 25 is deteriorated, a delay in response until a change of the atmosphere at the periphery of the downstream gas sensor 25 in a lean direction emerges as a change in the output of the downstream gas sensor 25 is increased. Therefore, the more deteriorated the response of the downstream gas sensor 25, the smaller the output change width (SOXa–SOXb) of the downstream gas sensor 25 until the predetermined time period T1 has elapsed from stopping the engine. Therefore, presence or absence of abnormality of the response of the downstream gas sensor 25 can be diagnosed by whether the output change width (SOXa–SOXb) of the downstream gas sensor 25 is smaller than the abnormality determinant OXd. Thereby, after stopping the engine, under a condition of excluding the influence of the storage effect of the catalyst 23, abnormality of the downstream gas sensor 25 can be diagnosed and accuracy of diagnosing abnormality of the downstream gas sensor 25 can be enhance. Further, abnormality of the downstream gas sensor 25 is diagnosed after stopping the engine. Therefore, adverse influence is not applied to exhaust emission or drivability at all.

Meanwhile, there is shown a change that after stopping the engine, the output of the downstream gas sensor 25 is gradually changed and converged to the atmospheric level by the back flow of the atmospheric air into the exhaust gas 22. When the output of the downstream gas sensor 25 has already become the lean value immediately before stopping the engine, the change width until the output of the downstream gas sensor 25 is changed to the atmospheric level after stopping the engine is reduced. Therefore, a difference of the change of the sensor output between the normal exhaust gas sensor and the abnormal (deteriorated) exhaust gas sensor is reduced and there is a possibility that the accuracy of diagnosing the abnormality of the downstream gas sensor 25 is deteriorated.

In this respect, according to the first embodiment, when the output SOXa of the downstream gas sensor 25 at stopping the engine is leaner than the predetermined value, it is determined that the change width of the output of the downstream gas sensor 25 after stopping the engine is small (accurate abnormality diagnosis is difficult), abnormality diagnosis of the downstream gas sensor 25 is prohibited. Therefore, the deterioration of the accuracy of diagnosing abnormality of the downstream gas sensor 25 can be prevented beforehand.

Further, according to the first embodiment, the abnormality determinant OXd used in diagnosing abnormality of the downstream gas sensor 25 is set in accordance with the output SOXa (gas concentration at the periphery) of the downstream gas sensor 25 at stopping the engine in consideration that the change (change speed, change width) until the output of the downstream gas sensor 25 is changed to the atmospheric level after stopping the engine is changed in accordance with the gas concentration at the periphery of the downstream gas sensor 25 at stopping the engine. Therefore, the abnormality determinant used in diagnosing abnormality of the downstream gas sensor 25 can properly be changed in correspondence with the change in the change of the output of the downstream gas sensor 25 after stopping the engine in accordance with the output SOXa (gas concentration at the periphery) of the downstream gas sensor 25 at stopping the engine and the accuracy of diagnosing abnormality of the downstream gas sensor 25 can be promoted.

However, it is not necessarily needed to set the abnormality determinant used in diagnosing abnormality of the downstream gas sensor 25 in accordance with the output SOXa of the downstream gas sensor 25 at stopping the engine but in order to simplify operation processing in diagnosing abnormality, the abnormality determinant may be constructed with a previously set fixed value.

Figure 4:
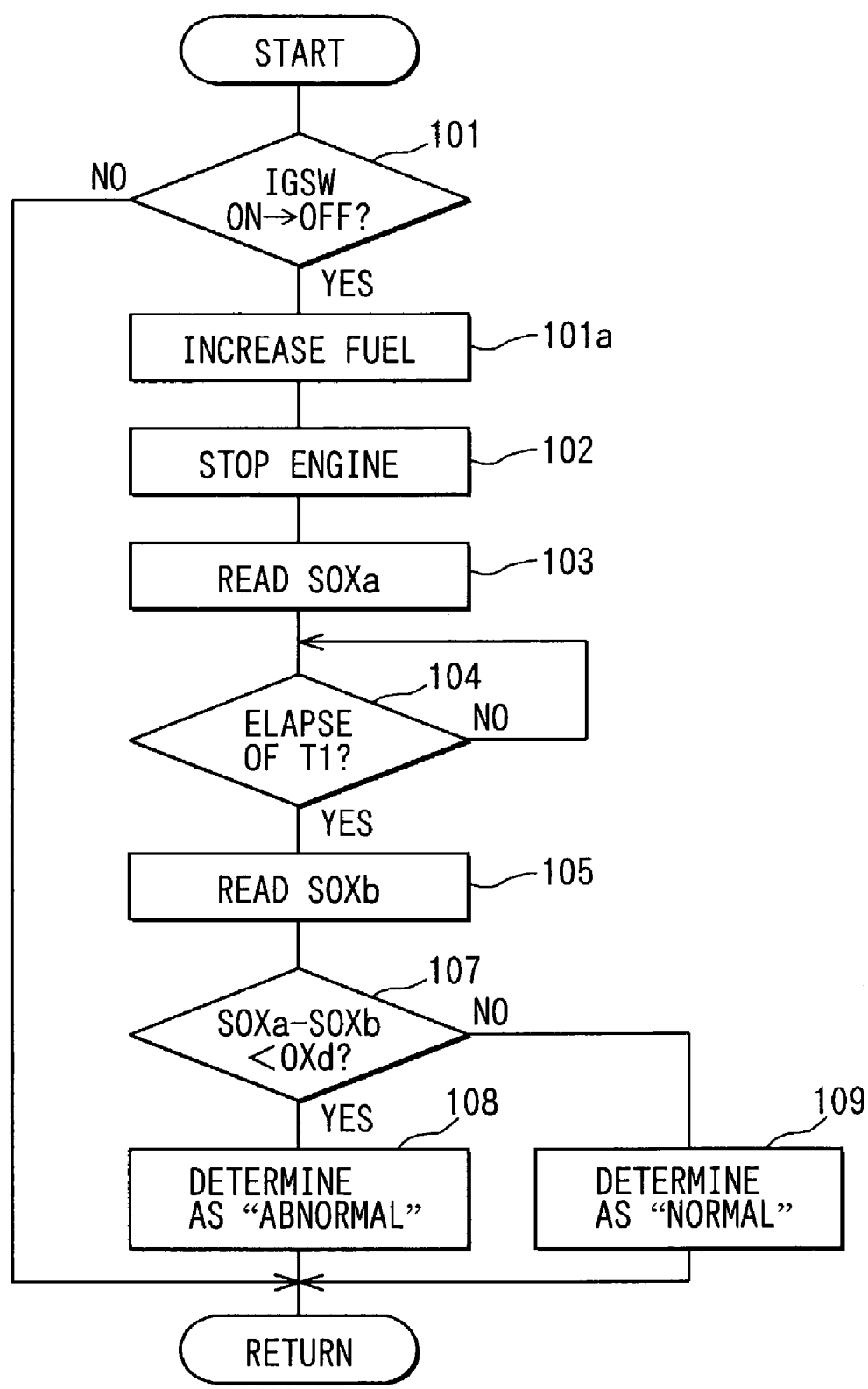
FIG. 4 is a flowchart showing a processing of an exhaust gas sensor abnormality diagnosing program according to a modification of the first embodiment.

Although according to the first embodiment, by prohibiting abnormality diagnosis of the downstream gas sensor 25 when the output SOXa of the downstream gas sensor 25 at stopping the engine is leaner than the predetermined value, the deterioration in the accuracy of diagnosing abnormality of the downstream gas sensor 25 is prevented, according to a modification of the first embodiment shown in FIG. 4, the deterioration in the accuracy of diagnosing abnormality of the downstream gas sensor 25 is prevented by correcting to increase the fuel injection amount immediately before stopping the engine.

According to the exhaust gas sensor abnormality diagnosis program of FIG. 4 executed in the modification, a processing of step 101a is added between steps 101 and 102 of the exhaust gas sensor abnormality diagnosis program of FIG. 2 described in the first embodiment, and a processing at step 106 of FIG. 2 is omitted.

According to the exhaust gas sensor abnormality diagnosis program of FIG. 4, at step 101, when it is determined that the ignition switch is switched from ON to OFF, the processing proceeds to step 101a and before stopping the engine 11, the fuel injection amount is corrected to increase and a rich component in the gas exhausted into the exhaust pipe 22 is increased immediately before stopping the engine to thereby change the output of the downstream gas sensor 25 to a rich direction. In this case, although an amount of correcting to increase the fuel injection amount may be a previously set fixed value for simplifying operation processing, the amount may be calculated by a map or an equation in accordance with a current fuel injection amount (target air/fuel ratio $\lambda$TG) or the output of the downstream gas sensor 25.

Thereafter, the engine 11 is stopped and the output SOXa of the downstream gas sensor 25 at stopping the engine and the output SOXb of the downstream gas sensor 25 after the predetermined time period T1 has elapsed from stopping the engine are read (steps 102 through 105), thereafter, the output change width (SOXa–SOXb) of the downstream gas sensor 25 until the predetermined time period T1 has elapsed from stopping the engine is calculated and presence or absence of abnormality of response of the downstream gas sensor 25 is determined by whether the output change width (SOXa–SOXb) is smaller than the abnormality determinant OXd (steps 107 through 109).

According to the modification, since the fuel injection amount is corrected to increase immediately before stopping the engine, even when the output of the downstream gas sensor 25 becomes a lean value comparatively proximate to the atmospheric level before stopping the engine, by correcting to increase the fuel injection amount immediately before stopping the engine, the output of the downstream gas sensor 25 is changed in the rich direction to thereby increase the change width until the output of the downstream gas sensor 25 is changed to the atmospheric level after stopping the engine and the deterioration in the accuracy of diagnosing the abnormality of the downstream gas sensor 25 can be prevented.

Further, although according to the first embodiment and the modification, the output change width (SOXa–SOXb) of the downstream gas sensor 25 until the predetermined time period T1 has elapsed from stopping the engine is compared with the abnormality determinant OXd to thereby diagnose presence or absence of abnormality of the downstream gas sensor 25, the method of diagnosing abnormality of the downstream gas sensor 25 may pertinently be changed.

For example, presence or absence of abnormality of response of the downstream gas sensor 25 may be diagnosed by measuring a time period required until the output of the downstream gas sensor 25 has changed to be equal to or smaller than a predetermined value from a time point of stopping the engine 11 and comparing the response time period with an abnormality determinant.

Further, presence or absence of abnormality of response of the downstream gas sensor 25 may be diagnosed by measuring a time period required until the output of the downstream gas sensor 25 has passed a predetermined section after stopping the engine and comparing the response time with an abnormality determinant.

Further, abnormality diagnosis of the exhaust gas sensor 24 on the upstream side of the catalyst 23 may be carried out by a method similar to those of the embodiment and the modification. However, the atmospheric air flowing back to the periphery of the exhaust gas sensor 24 on the upstream side of the catalyst 23 passes the catalyst 23. Therefore, a change in the output of the exhaust gas sensor 24 after stopping the engine is influenced by the storage effect of the catalyst 23. However, when a condition of determining abnormality diagnosis of the exhaust gas sensor 24 on the upstream side of the catalyst 23 is set by estimating the influence of the storage effect of the catalyst 23 from a deterioration determinant of the catalyst 23, abnormality of the exhaust gas sensor 24 on the upstream side of the catalyst 23 can be diagnosed after stopping the engine.

Alternatively, abnormality of the exhaust gas sensor 24 on the upstream side of the catalyst 23 may be diagnosed by whether the output of the exhaust gas sensor 24 on the upstream side of the catalyst 23 is at the atmospheric level when the periphery of the exhaust gas sensor 24 on the upstream side of the catalyst 23 is sufficiently filled with the atmosphere after stopping the engine.

(Second Embodiment)

Figure 6:
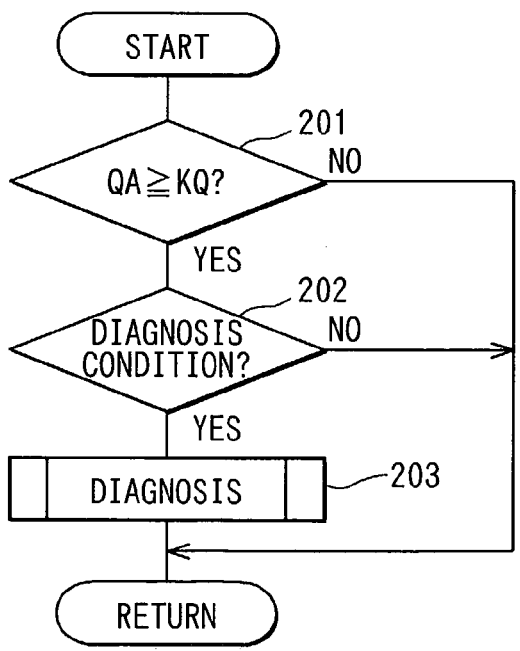
FIG. 6 is a flowchart showing a processing of an exhaust gas sensor abnormality diagnosing main routine according to a second embodiment of the present invention.
Figure 7:
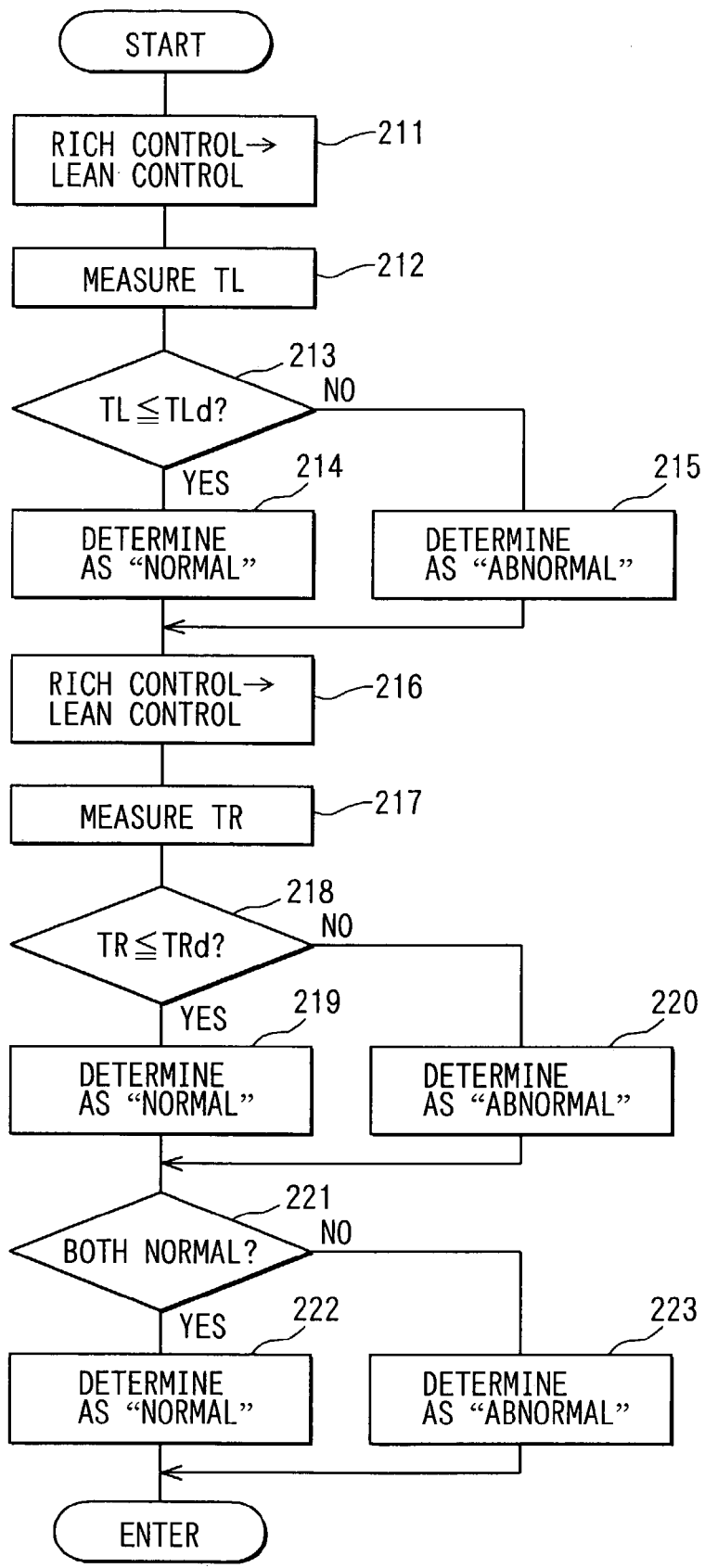
FIG. 7 is a flowchart showing a processing of an abnormality diagnosis execution subroutine in the second embodiment.

According to a second embodiment, ECU 28 executes abnormality diagnosis of the downstream gas sensor 25 based on the output of the exhaust gas sensor 25 on the downstream side of the catalyst 23 by switching rich/lean of an air/fuel ratio, when the intake air amount is equal to or larger than a predetermined abnormality diagnosis execution intake air amount KQ (intake air amount in correspondence with a lower limit value of a flow rate of exhaust gas exceeding cleaning function of the catalyst 23) by executing an exhaust gas sensor abnormality diagnosis main routine shown in FIG. 6 and an abnormality diagnosis execution subroutine shown in FIG. 7.

The exhaust gas sensor abnormality diagnosis main routine shown in FIG. 6 is executed at a predetermined period after turning an ignition switch (not illustrated) to ON. When the routine is started, first, at step 201, it is determined whether the intake amount QA detected by the air flow meter 14 is equal to or larger than the abnormality diagnosis execution intake air amount KQ. Here, the abnormality diagnosis execution intake air amount KQ is set to an intake air amount exceeding cleaning function of an undeteriorated catalyst (substantially new catalyst) in consideration of a difference in the cleaning function of the catalyst 23.

When the intake amount QA is smaller than the abnormality diagnosis execution intake air amount KQ, the program is finished as it is. Meanwhile, when it is determined that the intake amount QA is equal to or larger than the abnormality diagnosis execution intake air amount KQ, the processing proceeds to step 202 and it is determined whether an abnormality diagnosis execution condition of the downstream gas sensor 25 is established. Here, as the abnormality diagnosis execution condition of the downstream gas sensor 25, for example, all of the following conditions ① through ② are to be satisfied.

① The downstream gas sensor 25 is brought into an active state.

② The engine is in the warmed-up condition.

③ A variation in rotation of the engine falls in a predetermined range.

④ A variation in load of the engine falls in a predetermined range.

The above conditions of ① and ④ are conditions for bringing an engine operating state into a substantially steady state.

When any one of the above conditions ① through ④ is not satisfied, the abnormality diagnosis execution condition of the downstream gas sensor 25 is not established and the program is finished without executing abnormality diagnosis of the downstream gas sensor 25.

Meanwhile, when all of the above conditions of ① through ④ are satisfied, the abnormality diagnosis execution condition of the downstream gas sensor 25 is established and the processing proceeds to step 203 to execute the abnormality diagnosis execution subroutine shown in FIG. 7 and executes the abnormality diagnosis of the downstream gas sensor 25 as follows.

When abnormality diagnosis execution subroutine of FIG. 7 is started, first, at step 211, rich control for controlling an air/fuel ratio on the upstream side of the catalyst (target air/fuel ratio) to be richer than the stoichiometric air/fuel ratio (for example, target air/fuel ratio=14) is executed. After elapse of a sufficient time period for stabilizing the output of the downstream gas sensor 25 from starting the rich control, the rich control is switched to lean control for controlling the air/fuel ratio (target air/fuel ratio) on the upstream side of the catalyst to be leaner than the stoichiometric air/fuel ratio (for example, target air/fuel ratio=16).

Thereafter, the processing proceeds to step 212, measures a time period required to reach a time point t22 at which the output of the downstream gas sensor 25 is changed to be equal to or smaller than a predetermined value V1 from a time point t21 at which the rich control is switched to the lean control as a lean response time period TL (FIG. 8) and thereafter proceeds to step 213 to determine whether the lean response time period TL is equal to or smaller than a predetermined lean response determinant TLd.

When the lean response time period TL is equal to or smaller than the lean response determinant TLd, the processing proceeds to step 214 and determines that the lean response of the downstream gas sensor 25 is normal (not deteriorated). Meanwhile, when the lean response time period TL is longer than the lean response determinant TLd, the processing proceeds to step 215 and determines that the lean response of the downstream gas sensor 25 is abnormal (deteriorated).

Thereafter, the processing proceeds to step 216 and switches the lean control to the rich control after elapse of a time period sufficient for stabilizing the output of the downstream gas sensor 25 from starting the lean control.

Thereafter, the processing proceeds to step 217, measures a time period required to reach a time point T24 at which the output of the downstream gas sensor 25 is changed to be equal to or larger than the predetermined value V1 from a time point T23 at which the lean control is switched to the rich control and thereafter proceeds to step 218 to determine whether the rich response time period TR is equal to or smaller than a rich response determinant TRd.

When the rich response time TR is equal or smaller than the rich response determinant TRd, the processing proceeds to step 219 and determines that the rich response of the downstream gas sensor 25 is normal (not deteriorated). Meanwhile, when the rich response time period TR is longer than the rich response determinant TRd, the processing proceeds to step 220 and determines that the rich response of the downstream gas sensor 25 is abnormal (deteriorated).

Thereafter, the processing proceeds to step 221 and determines whether both of the lean response and the rich response of the downstream gas sensor 25 are normal. When the both are normal, the processing proceeds to step 222 to finally determine that the downstream gas sensor 25 is normal (not deteriorated). Meanwhile, when even either one of the lean response and the rich response of the downstream gas sensor 25 is determined to be abnormal (deteriorated), the processing proceeds to step 223 and finally determines that the downstream gas sensor 25 is abnormal (deteriorated). At this occasion, the downstream gas sensor 25 may be determined to be abnormal only when both of the lean response and the rich response are determined to be abnormal.

Figure 8:
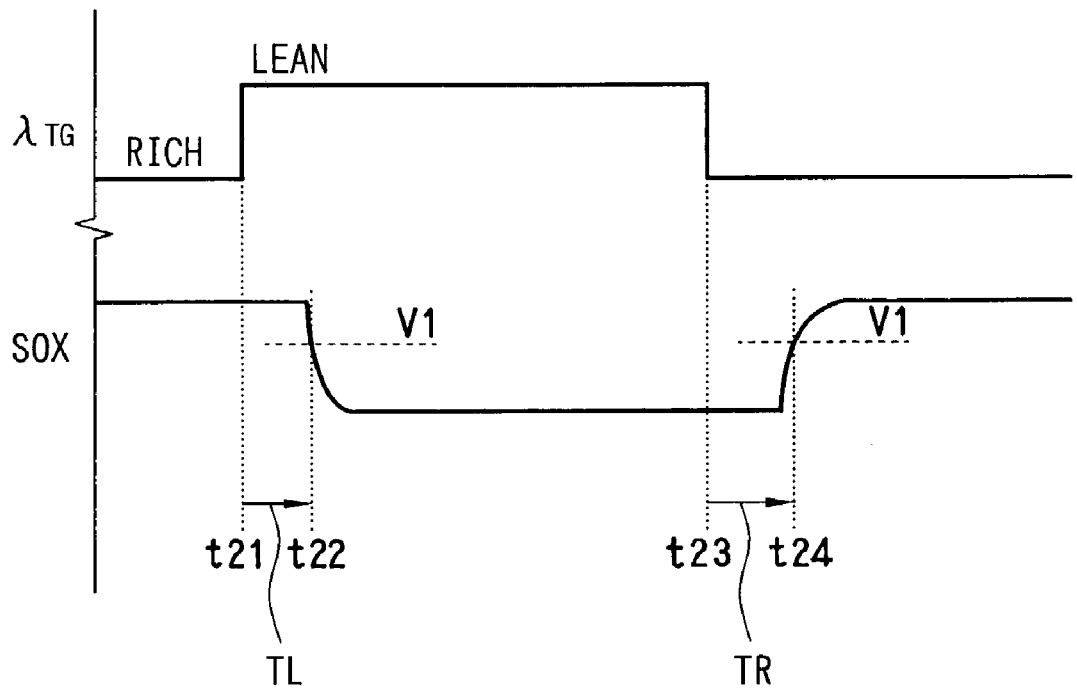
FIG. 8 is a time chart showing a method of diagnosing an abnormality of an exhaust gas sensor according to the second embodiment.

According to the second embodiment, as shown in FIG. 8, the time period required to reach the time point t22 at which the output of the downstream gas sensor 25 is changed to be equal to or smaller than the predetermined value V1 from the time point t21 at which the rich control is switched to the lean control is measured as the lean response time period TL and the time period required to reach the time point t24 at which the output of the downstream gas sensor 25 is changed to be equal to or larger than the predetermined value V1 from the time point t23 at which the lean control is changed to the rich control is measured as the rich response time TR.

Figure 9:
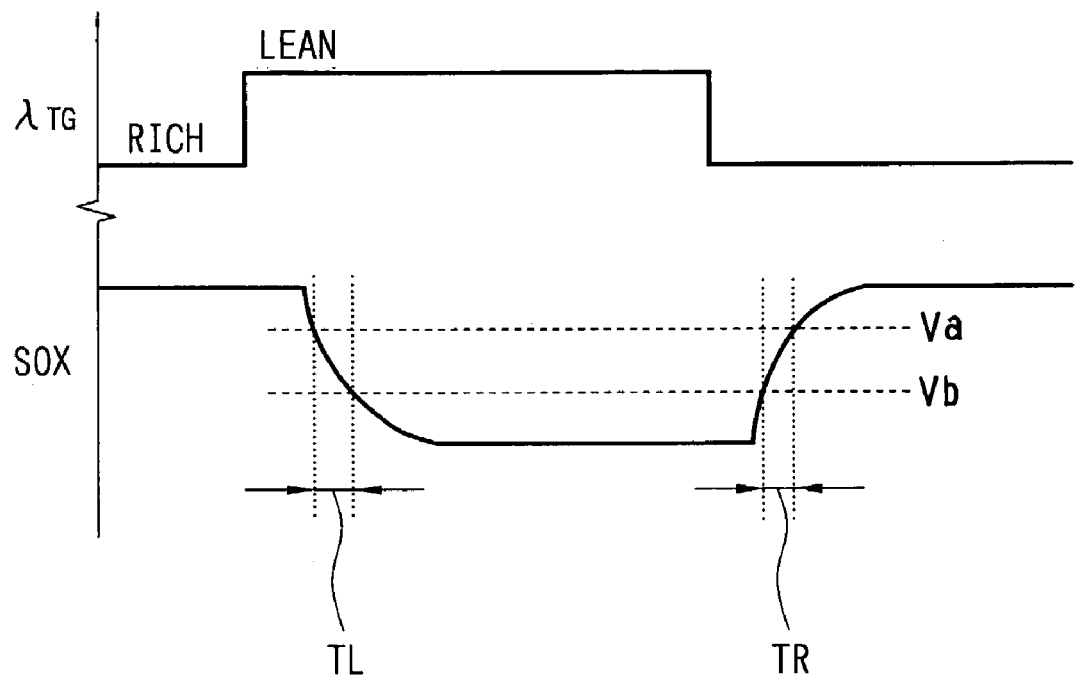
FIG. 9 is a time chart showing other method of diagnosing an abnormality of an exhaust gas sensor according to the second embodiment.

However, as shown in FIG. 9, when the rich control is switched to the lean control, a time period required for the output of the downstream gas sensor 25 to pass a predetermined interval Va through Vb (when the downstream gas sensor 25 is an oxygen sensor, for example, an interval of 0.7V through 0.2V) may be measured as the lean response time TL. Thereafter, when the lean control is switched to the rich control, a time period required for the output of the downstream gas sensor 25 to pass a predetermined interval of Vb through Va (when the downstream gas sensor 25 is an oxygen sensor, for example, an interval of 0.2V through 0.7V) may be measured as the rich response time TR. Further, determinant voltage V1 (Va through Vb) for measuring the lean response time period TL and determinant voltage V1 (Vb through Va) for measuring the rich response time period TR may be set to voltages different from each other.

Figure 5:
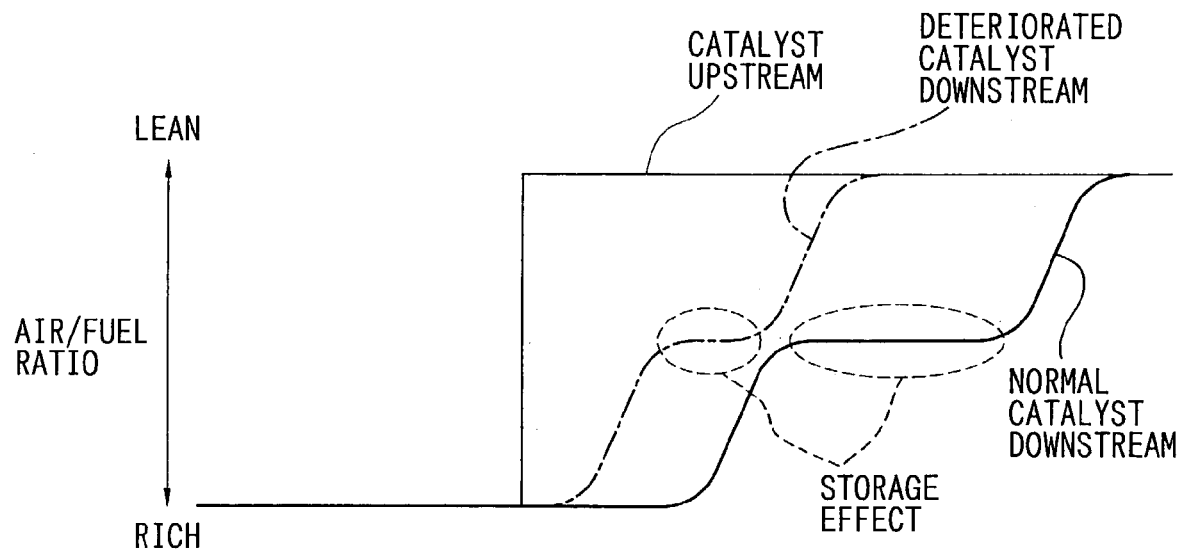
FIG. 5 is a time chart showing an influence of a storage effect of a catalyst and presence or absence of deterioration in the catalyst on a change of an air/fuel ratio on a downstream side of the catalyst.
Figure 10A:
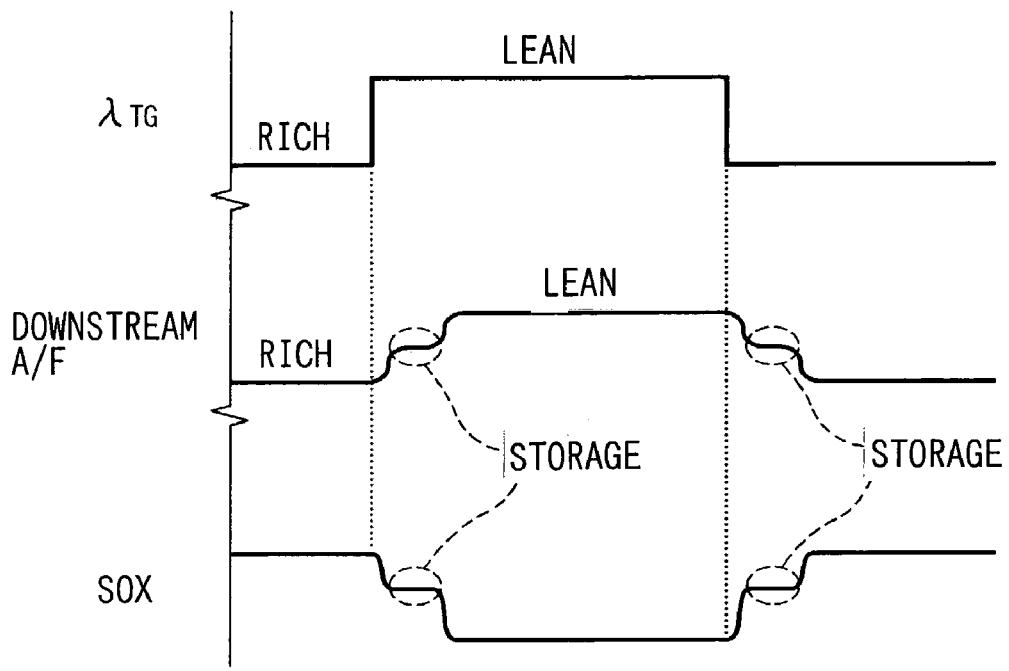
FIG. 10A is a time chart showing an operation of the second embodiment when an intake air amount is smaller than an abnormality diagnosis execution intake air amount.

As shown in FIG. 10A, when the intake air amount is small (smaller than the abnormality diagnosis execution intake air amount KQ), there is a delay time period during which an air/fuel ratio on the downstream side of the catalyst hardly changes even when an air/fuel ratio (A/F) on the upstream side of the catalyst (target A/F) is switched, the delay time period (duration time period of the storage effect) is changed by a degree of deterioration of the catalyst 23 (FIG. 5). Therefore, the response time period of the downstream gas sensor 25 is changed by being influenced by the storage effect of the catalyst 23 and presence or absence of abnormality of the downstream gas sensor 25 cannot accurately be determined.

Figure 10B:
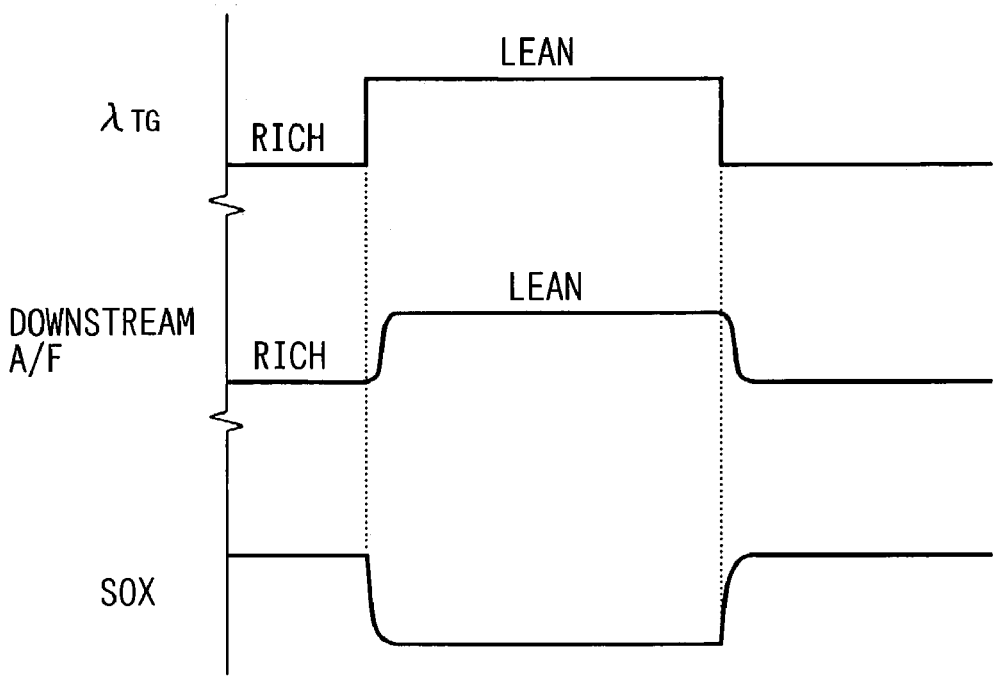
FIG. 10B is a time chart showing an operation of the second embodiment when the intake air amount is larger than the abnormality diagnosis execution intake air amount.

In contrast thereto, according to the second embodiment, as shown in FIG. 10B, when the intake air amount is large, specifically, equal to or larger than the abnormality diagnosis execution intake air amount KQ, abnormality of the downstream gas sensor 25 is diagnosed by switching the air/fuel ratio on the upstream side of the catalyst (target air/fuel ratio) and measuring the response time of the downstream gas sensor 25. When the intake air amount is equal to or larger than the abnormality diagnosis execution intake air amount KQ, a storage amount (adsorbed amount) of the lean component or the rich component of the catalyst 23 is brought into the saturated state, exhaust gas passing through the catalyst 23 without being cleaned thereby is increased. Therefore, when the air/fuel ratio on the upstream side of the catalyst (target air/fuel ratio) is switched under the state, a change in the air/fuel ratio on the upstream side of the catalyst emerges as a change in the air/fuel ratio on the downstream side of the catalyst with excellent response without hardly undergoing the influence of the storage effect of the catalyst 23. Thereby abnormality of the downstream gas sensor 25 can be diagnosed based on the output of the downstream gas sensor 25 under the condition of substantially excluding the influence of the storage effect of the catalyst 23 and presence or absence abnormality of the downstream gas sensor 25 can accurately be determined.

According to the second embodiment, the abnormality diagnosis execution intake air amount KQ is set to the intake air amount exceeding the cleaning function of the undeteriorated catalyst (substantially new catalyst) in consideration of the difference in the cleaning function of the catalyst 23. However, depending on a method of operating the vehicle or road situation, the frequency of executing abnormality diagnosis of the downstream gas sensor 25 may be reduced since the frequency of operation in which the intake air amount becomes equal to or larger than the abnormality diagnosis execution intake air amount KQ is reduced.

Figure 11:
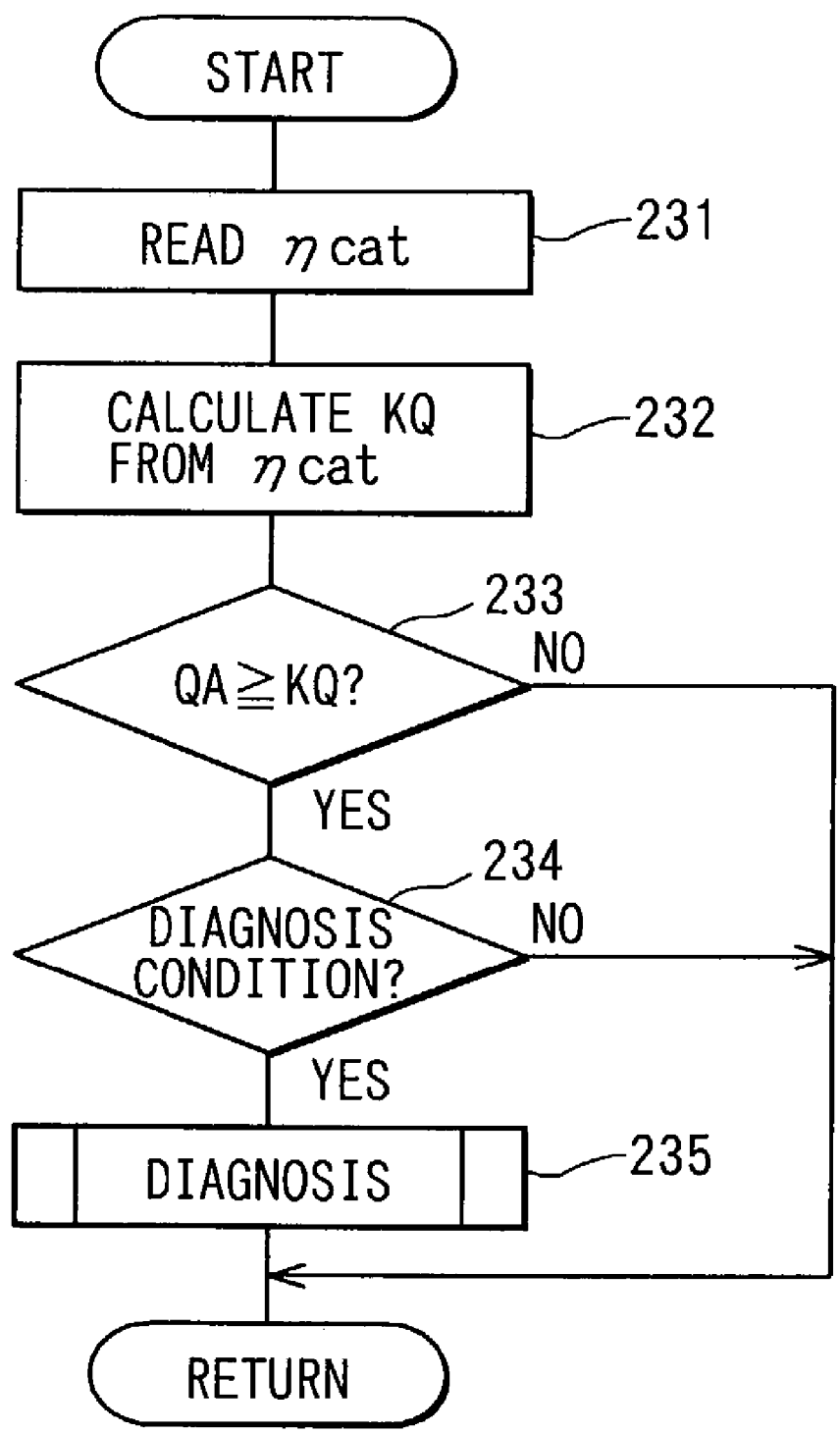
FIG. 11 is a flowchart showing a processing of an exhaust gas sensor abnormality diagnosis main routine according to a first modification of the second embodiment.
Figure 12:
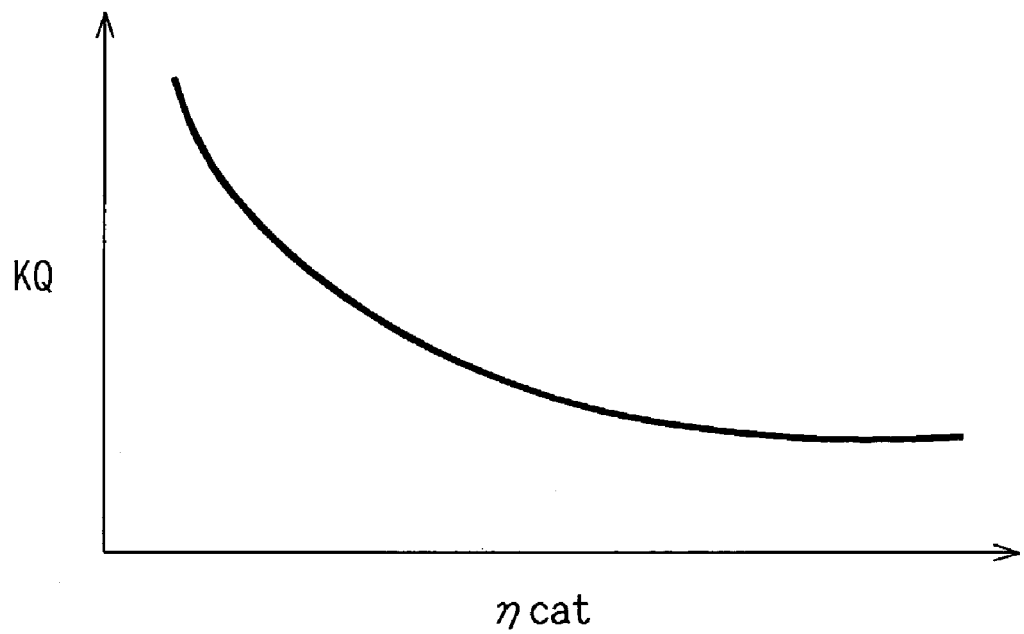
FIG. 12 is a graph showing a map for specifying a relationship between a degree of deteriorating a catalyst and an abnormality diagnosis execution intake air amount.

Hence, according to a first modification of the second embodiment shown in FIG. 11 and FIG. 12, a degree ηcat of deterioration of the catalyst 23 is detected and the abnormality diagnosis execution intake air amount KQ is set in accordance with the degree ηcat of the deterioration of the catalyst 23 in consideration of the fact that the more progressed is the degree ηcat of deterioration of the catalyst 23, the more deteriorated is the cleaning function (storage effect) of the catalyst 23 and the smaller the flow rate of exhaust gas (intake air amount) capable of being cleaned by the catalyst 23.

The processing of an exhaust gas sensor abnormality diagnosis main routine of FIG. 11 will be described as follows. When the routine is started, first, at step 231, the degree ηcat of deterioration of the catalyst 23 is read. As the degree ηcat of deterioration of the catalyst 23, there is used a degree of deterioration of the catalyst 23 calculated for determining presence or absence of deterioration of the catalyst 23 by a catalyst deterioration diagnosis program, not illustrated.

Thereafter, the processing proceeds to step 232, searches a map of the abnormality diagnosis execution intake air amount KQ with the degree ηcat of deterioration of the catalyst 23 shown in FIG. 12 as a parameter and calculates the abnormality diagnosis execution intake air amount KQ in accordance with the current degree ηcat of deterioration of the catalyst 23.

The map of the abnormality diagnosis execution intake air amount KQ is set such that the more progressed is the degree ηcat of deterioration of the catalyst 23, the smaller the abnormality diagnosis execution intake air amount KQ. Thereby, the more progressed the degree ηcat of deterioration of the catalyst 23 (the smaller the flow rate of the exhaust gas capable of being cleaned by the catalyst 23), to the smaller value the abnormality diagnosis execution intake air amount KQ is set to thereby enlarge a range of the intake air amount for executing the abnormality diagnosis of the downstream gas sensor 25 to a range of a smaller intake air amount.

After calculating the abnormality diagnosis execution intake air amount KQ, the processing proceeds to step 233, determines whether the intake air amount detected by the air flow meter 14 is equal to or larger than the abnormality diagnosis execution intake air amount KQ and determines whether the conditions of executing abnormality diagnosis of the downstream gas sensor 25 are established at successive step 234.

When it is determined that the intake air amount is equal to or larger than the abnormality diagnosis execution intake air amount KQ and the conditions of executing the abnormality diagnosis of the downstream gas sensor 25 are established, the processing proceeds to step 235, executes the abnormality diagnosis execution subroutine of FIG. 7 and executes abnormality diagnosis of the downstream gas sensor 25 by a method the same as that of the second embodiment.

According to the first modification, the more progressed is the degree ηcat of deterioration of the catalyst 23, to the smaller value the abnormality diagnosis execution intake air amount KQ is set in consideration of a situation that the more progressed is the degree ηcat of deterioration of the catalyst 23, the more deteriorated is the cleaning function (storage effect) of the catalyst 23 and the smaller the flow rate of exhaust gas (intake air amount) capable of being cleaned by the catalyst 23. Therefore, the frequency of the operation in which the intake air amount becomes equal to or larger than the abnormality diagnosis execution intake air amount KQ in accordance with the degree ηcat of deterioration of the catalyst 23 can be increased to thereby increase the frequency of executing the abnormality diagnosis of the downstream gas sensor 25.

Figure 13:
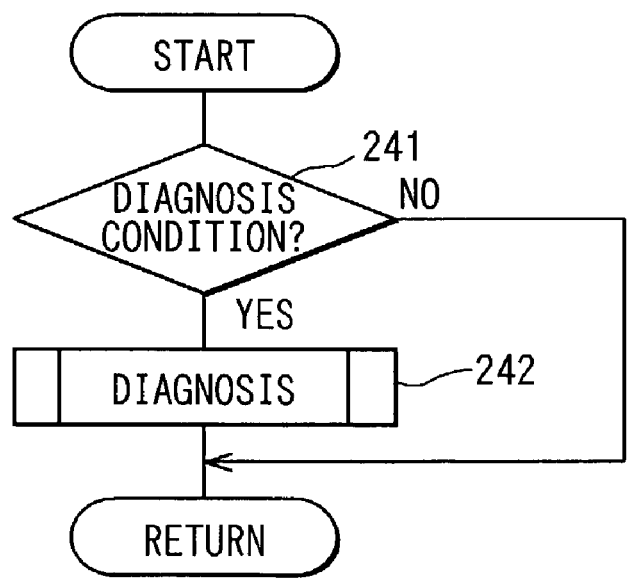
FIG. 13 is a flowchart showing a processing of an exhaust gas sensor abnormality diagnosis main routine according to a second modification of the second embodiment.
Figure 14:
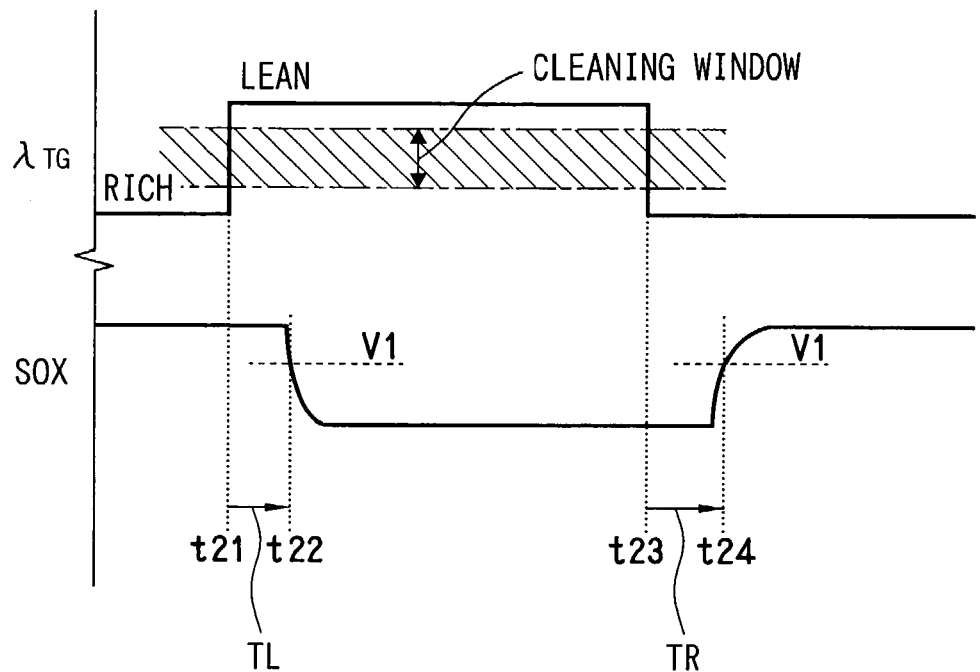
FIG. 14 is a time chart showing a method of diagnosing an abnormality of an exhaust gas sensor according to the second modification.
Figure 15:
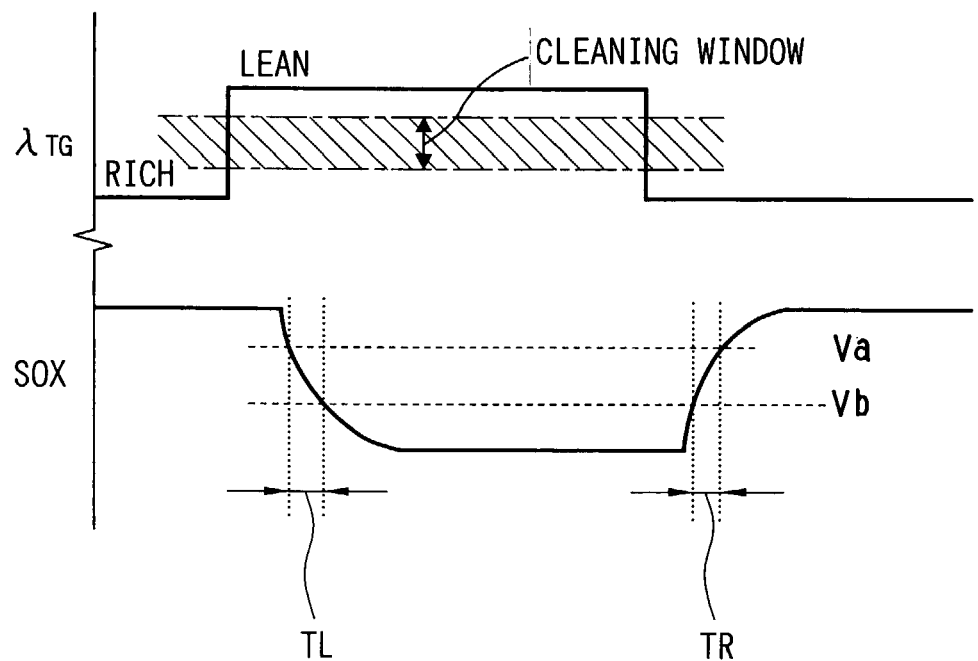
FIG. 15 is a time chart showing other method of diagnosing an abnormality of an exhaust gas sensor according to the second modification.

According to a second modification shown in FIG. 13 through FIG. 15, in consideration of a characteristic of the cleaning rate of the catalyst 23 (characteristic in which the cleaning rate, that is, cleaning capability) is increased in a predetermined air/fuel range referred to as cleaning window and the cleaning rate is extremely reduced at the other air/fuel ratio), when the air/fuel ratio on the upstream side of the catalyst (target air/fuel ratio) becomes an air/fuel ratio exceeding the cleaning function of the catalyst 23 (air/fuel ratio other than cleaning window), abnormality diagnosis of the downstream gas sensor 25 is executed by switching rich/lean of the air/fuel ratio on the upstream side of the catalyst (target air/fuel ratio) to exceed the cleaning function of the catalyst 23.

The processing of an exhaust gas sensor abnormality diagnosis main routine of FIG. 13 is executed in the second modification will be described. When the routine is started, first, at step 241, it is determined whether the conditions of executing abnormality diagnosis of the downstream gas sensor 25 are established. When the conditions of executing abnormality diagnosis are established, the processing proceeds to step 242, executes the abnormality diagnosis execution subroutine of FIG. 7 and executes abnormality diagnosis of the downstream gas sensor 25.

At the occasion, as shown in FIG. 14, when the air/fuel ratio on the upstream side of the catalyst becomes an air/fuel ratio exceeding the cleaning function of the catalyst 23 (air/fuel ratio other than cleaning window), in order to switch rich/lean of the air/fuel ratio on the upstream side of the catalyst, during the rich control, the air/fuel ratio on the upstream side of the catalyst (target air/fuel ratio) is controlled to a rich side of the cleaning window of the catalyst 23 (for example, target air/fuel ratio=12). During the lean control, the air/fuel ratio on the upstream side of the catalyst (target air/fuel ratio) is controlled to a lean side of the cleaning window of the catalyst 23 (for example, target air/fuel ratio=17).

Further, a time period required to reach the time point t22 at which the output of the downstream gas sensor 25 is changed to be equal to or smaller than the predetermined value V1 from the time point t21 at which the rich control is switched to the lean control is measured as the lean response time period TL and the lean response time period TL is compared with the lean response determinant to thereby determine presence or absence of abnormality of the lean response of the downstream gas sensor 25.

Thereafter, the time period required to reach the time point t24 at which the output of the downstream gas sensor 25 is changed to be equal to or larger than the predetermined value V1 from the time point t23 at which the lean control is switched to the rich control is measured as the rich response time period TR and the rich response time period TR is compared with the rich response determinant to thereby determine presence or absence of abnormality of the rich response of the downstream gas sensor 25.

Further, as shown in FIG. 15, when the rich control is switched to the lean control, the time period required for the output of the downstream gas sensor 25 to pass a predetermined section Va through Vb (when the downstream gas sensor 25 is an oxygen sensor, for example, an interval of 0.7V through 0.2V) maybe measured as the lean response time period TL. Thereafter, when the lean control is switched to the rich control, the time period required for the output of the downstream gas sensor 25 to pass a predetermined interval of Vb through Va (when the downstream gas sensor 25 is an oxygen sensor, for example, an interval of 0.2V through 0.7V) may be measured as the rich response time period TR. Further, the determinant voltage V1 (Va through Vb) for measuring the lean response time period TL and the determinant voltage V1 (Vb through Va) for measuring the rich response time period TR may be set to voltages different from each other.

According to the second modification, when the air/fuel ratio on the upstream side of the catalyst (target air/fuel ratio) becomes the air/fuel ratio exceeding the cleaning function of the catalyst 23 (air/fuel ratio other than cleaning window), abnormality diagnosis of the downstream gas sensor 25 is executed by switching rich/lean of the air/fuel ratio on the upstream side of the catalyst (target air/fuel ratio) to exceed the cleaning function of the catalyst 23. At the air/fuel ratio exceeding the cleaning function of the catalyst 23 (air/fuel ratio other than cleaning window of catalyst 23) a component of exhaust gas passing through the catalyst 23 without being cleaned thereby is increased. Therefore, when rich/lean of the air/fuel ratio of the upstream side of the catalyst is switched under the state, the change in the air/fuel ratio on the upstream side of the catalyst emerges as the change in the air/fuel ratio on the downstream side of the catalyst with excellent response without hardly undergoing the influence of the storage effect of the catalyst 23 and abnormality diagnosis of the downstream gas sensor 25 can accurately be carried out.

Further, according to the second embodiment and the modifications, when the intake amount QA is equal to or larger than the abnormality diagnosis execution intake air amount KQ and the air/fuel ratio on the upstream side of the catalyst (target air/fuel ratio) becomes the air/fuel ratio exceeding the cleaning function of the catalyst 23 (air/fuel ratio other than cleaning window), abnormality diagnosis of the downstream gas sensor 25 may be executed by switching rich/lean of the air/fuel ratio on the upstream side of the catalyst (target air/fuel ratio) to exceed the cleaning function of the catalyst 23.

The method of diagnosing abnormality of the downstream gas sensor 25 may be changed. For example, a deterioration in the response of the downstream gas sensor 25 may be diagnosed by calculating an average lean response time period and an average rich response time period of the downstream gas sensor 25 when rich/lean of the air/fuel ratio is alternately switched at a constant period and comparing respectively the average lean response time period and the average rich response time period with determinants.

Further, the deterioration in the response of the downstream gas sensor 25 may be diagnosed based on a ratio of frequencies or a ratio of amplitudes of the output of the upstream side exhaust gas sensor 24 and the output of the downstream gas sensor 25 when rich/lean of the air/fuel ratio is alternately switched at a constant period.

(Third Embodiment)

Figure 16:
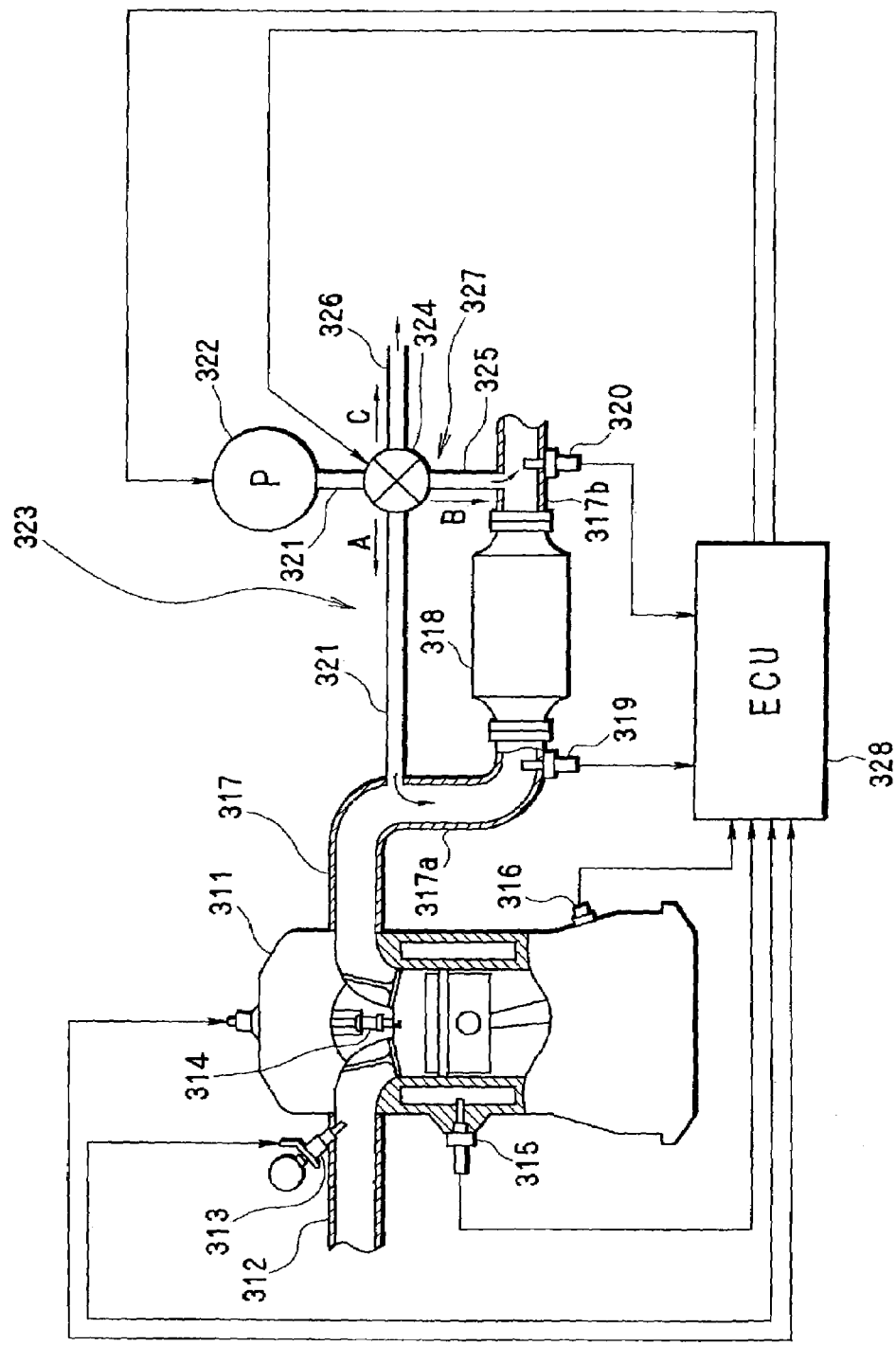
FIG. 16 is a schematic view of an engine control system according to a third embodiment of the invention.

According to the third embodiment, as shown in FIG. 16, a fuel injection valve 313 for respectively injecting fuel is attached to a vicinity of an intake port of an intake manifold 312 for introducing air to each cylinder of an internal combustion engine 311. Further, a cylinder head of the engine 311 is attached with an ignition plug 314 for each cylinder and mixture gas in the cylinder is ignited by spark discharge of each ignition plug 314. Further, a cylinder block of the engine 311 is attached with a cooling water sensor 315 for detecting cooling water temperature and a crank angle sensor 316 for detecting engine rotational speed NE.

Meanwhile, an exhaust pipe 317 (exhaust path) of the engine 311 is installed with a catalyst 318 of a three-way catalyst for cleaning CO, HC and NOx in exhaust gas and exhaust gas sensors 319 and 320 (air/fuel ratio sensor, oxygen sensor) for respectively detecting air/fuel ratio or lean/rich of exhaust gas are installed on the upstream side and the downstream side of the catalyst 318.

Further, a secondary air introducing pipe 321 for introducing outside air as the secondary air is connected to an exhaust pipe 317a on the upstream side of the catalyst 318 and an air pump 322 for pressurizing the secondary air is installed at the most upstream portion of the secondary air introducing pipe 321. The air pump 322 is driven by an actuator of a motor or the like or engine power. A the secondary air introducing apparatus 323 is constructed with the secondary air introducing pipe 321 and the air pump 322.

Further, an abnormality diagnosing gas introducing pipe 325 and an atmosphere opening pipe 326 are connected to a middle of the secondary air introducing pipe 321 of the secondary air introducing apparatus 323 via a the secondary air switch valve 324 and a downstream side end portion of the abnormality diagnosing gas introducing pipe 325 is connected to an upstream side of the downstream side discharge gas sensor 320 of an exhaust pipe 317b on the downstream side of the catalyst 318. An abnormality diagnosing gas introducing apparatus 327 is constructed with the secondary air introducing apparatus 323, the secondary air switch valve 324, the abnormality diagnosing gas introducing pipe 325 and the atmosphere opening pipe 326.

In this case, when the secondary air switch valve 324 is switched to the secondary air introducing position, as shown by arrow mark A in FIG. 16, the secondary air pressurized by the air pump 322 is introduced into the catalyst upstream side exhaust pipe 317a by passing the secondary air introducing pipe 321. Meanwhile, when the secondary air switch valve 324 is switched to an abnormality diagnosing gas introducing position, as shown by an arrow mark B, the secondary air pressurized in the air pump 322 is introduced to the upstream side of the downstream side discharge gas sensor 320 in the catalyst downstream side exhaust pipe 317b by passing the abnormality diagnosing gas introducing pipe 325 as an abnormality diagnosing gas. Further, when the secondary air switch valve 324 is switched to an atmosphere opening position, as shown by an arrow mark C, the secondary air pressurized by the air pump 322 is discharged into the atmosphere by passing the atmosphere opening pipe 326.

Outputs of the various sensors are inputted to an engine control circuit (ECU) 328.

Figure 17:
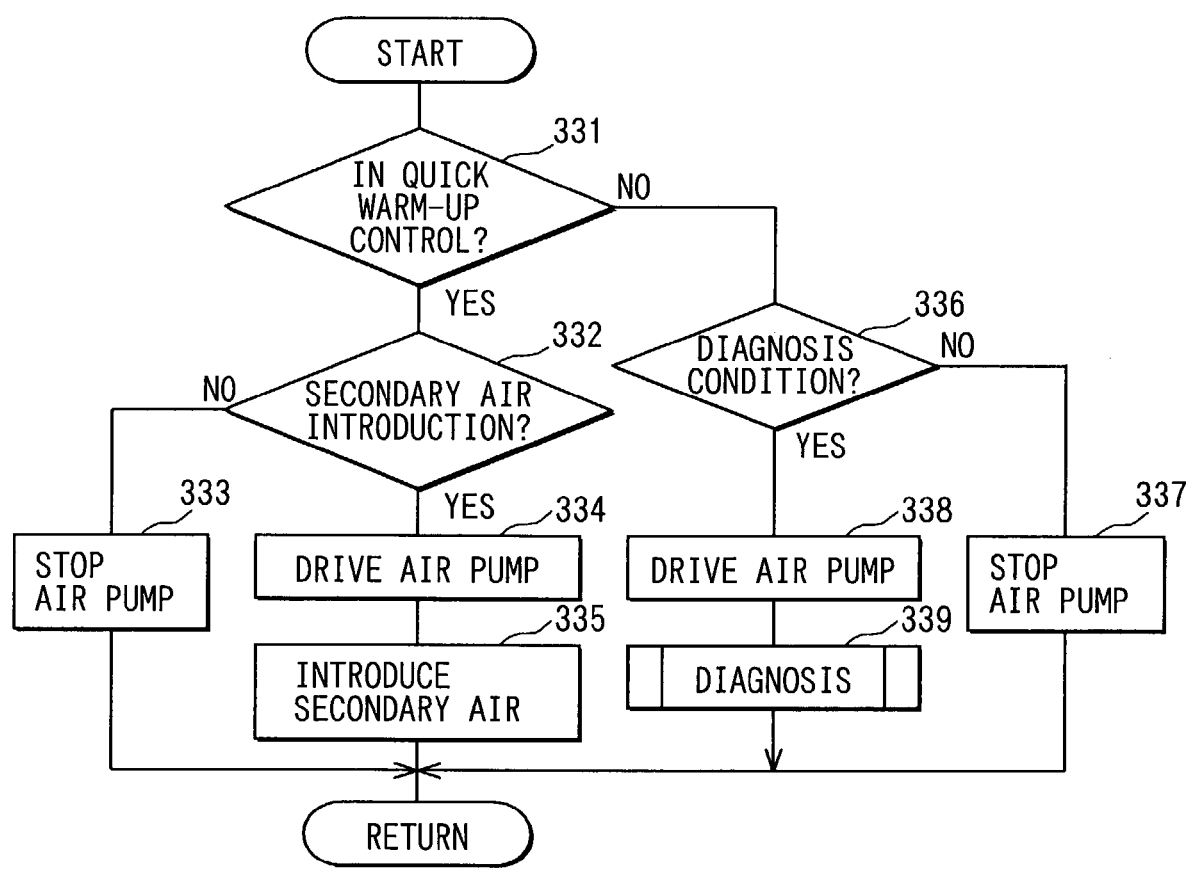
FIG. 17 is a flowchart showing a processing of a the secondary air introduction control and an exhaust gas sensor abnormality diagnosis routine in the third embodiment.

Further, by executing the secondary air introducing control and exhaust gas sensor abnormality diagnosing routine shown in FIG. 17, when conditions of introducing the secondary air are established in executing catalyst quick warm-up control, ECU 328 introduces the secondary air into the catalyst upstream side exhaust pipe 317a. When the catalyst quick warm-up control is not executed, in the case in which the conditions of executing abnormality diagnosis of the downstream gas sensor 320 are established, ECU 328 executes an abnormality diagnosis execution subroutine shown in FIG. 18, switches a state of introducing the secondary air (abnormality diagnosing gas) into the catalyst downstream side exhaust pipe 317b and a state of stopping to introduce the secondary air therein, and executes abnormality diagnosis of the downstream gas sensor 325 based on a change of an output of the downstream gas sensor 320 brought about at the occasion.

The secondary air introducing control and discharge gas sensor abnormality diagnosing routine shown in FIG. 17 is executed at a predetermined period after making an ignition switch (not illustrated) ON. When the program is started, first, at step 331, it is determined whether the catalyst quick warm-up control is being executed. In executing the catalyst quick warm-up control, exhaust gas temperature is elevated by carrying out, for example, an igniting time point delay angle control.

When it is determined that the catalyst quick warm-up control is being executed, the processing proceeds to step 332 to determine whether the conditions of introducing the secondary air have been established here. Here, for example, all of the following conditions ① through ③ should be satisfied as the conditions for introducing the secondary air.

① Cooling water temperature in starting falls in a predetermined range.

② Current cooling water temperature falls in a predetermined range.

③ Catalyst temperature is equal to or higher than a predetermined temperature (temperature capable of reacting a rich component in exhaust gas with the secondary air).

When any one of the conditions ① through ③ is not satisfied, the conditions of introducing the secondary air are not established. The processing proceeds to step 333 to make the air pump 322 remain in a stopped state and finishes the routine.

Meanwhile, when it is determined that the conditions of introducing the secondary air are established by satisfying all of the conditions ① through ③, the processing proceeds to step 334, drives the air pump 322 and switches the secondary air switch valve 324 to the secondary air introducing position at step 335 to thereby introduce the secondary air pressurized by the air pump 322 from the secondary air introducing pipe 321 into the catalyst upstream side exhaust pipe 317a as shown by the arrow mark A of FIG. 16. Thereby, the rich component (HC, CO) in the exhaust gas is reacted with the secondary air (oxygen) in the catalyst 318 and warms up the catalyst 318 in a short period of time by the reaction heat.

Further, the position of introducing the secondary air from the secondary air introducing pipe 321 into the catalyst upstream side exhaust pipe 317a may be set to a position on the upstream side at which exhaust gas temperature in the catalyst upstream side exhaust pipe 317a becomes equal to or higher than temperature to be able to combust the rich component in the exhaust gas (for example, 700° C.) and after burning may be brought about by mixing the rich component in exhaust gas at high temperature with the secondary air in the catalyst upstream side exhaust pipe 317a to thereby warm up the catalyst 318 in a short period of time by the combustion heat.

Meanwhile, at step 331, when it is determined that the catalyst quick warm-up control is not executed, the processing proceeds to step 336 and determines whether the conditions of executing abnormality diagnosis of the downstream gas sensor 320 are established. Here, for example, all of the following conditions (① through ④) should be satisfied as the conditions for executing abnormality diagnosis of the downstream gas sensor 320.

① The downstream gas sensor 320 is brought into an activated state.

② The engine 311 is brought into a state of finishing to warm up.

③ A variation in engine rotation falls in a predetermined range.

④ A variation in engine load falls in a predetermined range.

The above conditions of ③ and ④ are conditions for stabilizing an air/fuel ratio of exhaust gas by bringing an engine operating state substantially into a steady state.

When any one of the conditions ① through ④ is not satisfied, the conditions of executing abnormality diagnosis of the downstream gas sensor 320 are not established and the processing proceeds to step 337 to make the air pump 332 in the stopped state and finishes the routine.

Meanwhile, when it is determined that the conditions of executing abnormality diagnosis of the downstream gas sensor 320 are established by satisfying all the conditions of ① through ④, the processing proceeds to step 338, operates the air pump 332 and executes the abnormality diagnosis execution subroutine shown in FIG. 18 at successive step 339 and executes abnormality diagnosis of the downstream gas sensor 320 as follows.

Figure 18:
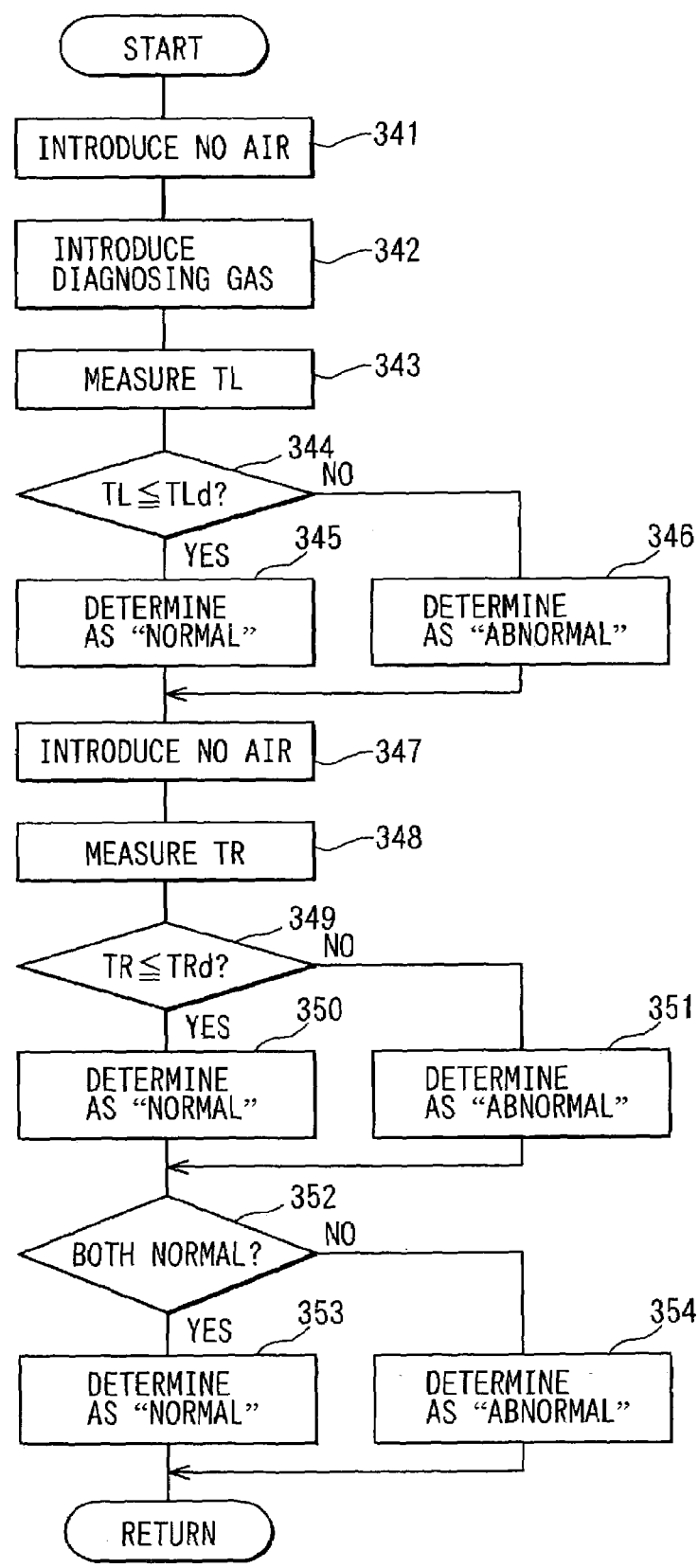
FIG. 18 is a flowchart showing a processing of an abnormality diagnosis execution subroutine.

When the abnormality diagnosis execution subroutine of FIG. 18 is started, first, at step 341, no secondary air is introduced (OFF). That is, the secondary air switch valve 324 is switched to the atmosphere opening position and, as shown by the arrow mark C of FIG. 16, the secondary air pressurized by the air pump 322 is discharged from the atmosphere opening pipe 326 to the atmosphere.

Thereafter, the processing proceeds to step 342, switches the secondary air switch valve 324 from the atmosphere opening position to the abnormality diagnosing gas introducing position after elapse of a time period necessary for stabilizing supply of the secondary air from starting to operate the air pump 322 and introduces the secondary air pressurized by the air pump 322 from the abnormality diagnosing gas introducing pipe 325 into the catalyst downstream side exhaust pipe 317b as abnormality diagnosing gas as shown by the arrow mark B of FIG. 16. That is diagnosing gas is ON. Thereby, an air/fuel ratio of exhaust gas flowing at the periphery of the downstream side discharge gas sensor 320 is changed to a lean direction.

Figure 19:
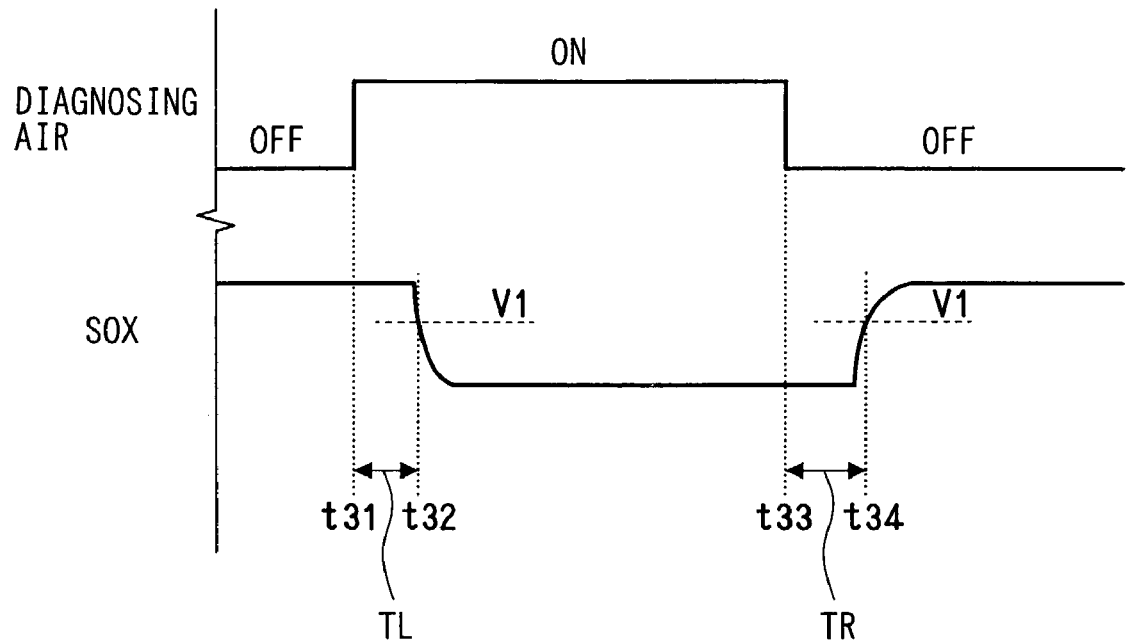
FIG. 19 is a time chart showing a method of diagnosing an abnormality of an exhaust gas sensor.

Thereafter, the processing proceeds to step 343, measures a time period required to reach a time point t32 at which the output of the downstream gas sensor 320 is changed to be equal to or smaller than the predetermined value V1 from a time point t31 at which the secondary air switch valve 324 is switched to the abnormality diagnosing gas introducing position as a lean response time period TL (FIG. 19) and thereafter proceeds to step 344 to determine whether the lean response time period TL is equal to or shorter than a predetermined lean response determinant TLd.

When the lean response time period TL is equal to or shorter than the lean response determinant TLd, the processing proceeds to step 345 and determines that the lean response of the downstream gas sensor 320 is normal (not deteriorated). Meanwhile, when the lean response time period TL is longer than the lean response determinant TLd, the processing proceeds to step 346 to determine that the lean response of the downstream gas sensor 320 is abnormal (deteriorated).

Thereafter, the processing proceeds to step 347, switches the secondary air switch valve 324 from the abnormality diagnosing gas introducing position to the atmosphere opening position after elapse of a time period necessary for stabilizing the output of the downstream gas sensor 320 and discharges the secondary air pressurized by the air pump 322 from the atmosphere opening pipe 326 into the atmosphere. Thereby, the secondary air (abnormality diagnosing gas) is stopped from being introduced into the catalyst downstream side exhaust pipe 317b and the air/fuel ratio of the exhaust gas flowing at a periphery of the downstream gas sensor 320 is changed into a direction of a stoichiometric air/fuel ratio.

Thereafter, the processing proceeds to step 348, calculates a time period required to reach a time point t34 at which the output of the downstream gas sensor 320 is changed to be equal to or larger than the predetermined value V1 from a time point t33 at which the secondary air switch valve 324 is switched to the atmosphere opening position as the rich response time period TR (FIG. 19) and thereafter proceeds to step 349 to determine whether the rich response time period TR is equal to or shorter than a rich response determinant TRd.

When the rich response time period TR is equal to or shorter than the rich response determinant TRd, the processing proceeds to step 350 and determines that the rich response of the downstream gas sensor 320 is normal (not deteriorated). Meanwhile, when the rich response time period TR is longer than the rich response determinant TRd, the processing proceeds to step 351 to determine that the rich response of the downstream gas sensor 320 is abnormal (deteriorated).

Thereafter, the processing proceeds to step 352 to determine whether both of the lean response and the rich response of the downstream side discharge gas sensor 320 are normal and proceeds to step 353 when both are normal and finally determines that the downstream gas sensor 320 is normal (not deteriorated). Meanwhile, when it is determined that even either one of the lean response and the rich response of the downstream gas sensor 320 is abnormal (deteriorated), the processing proceeds to step 354 and finally determines that the downstream gas sensor 320 is abnormal (deteriorated). In this case, the downstream gas sensor 320 may finally be determined to be abnormal only when both of the lean response and the rich response are abnormal.

Figure 20:
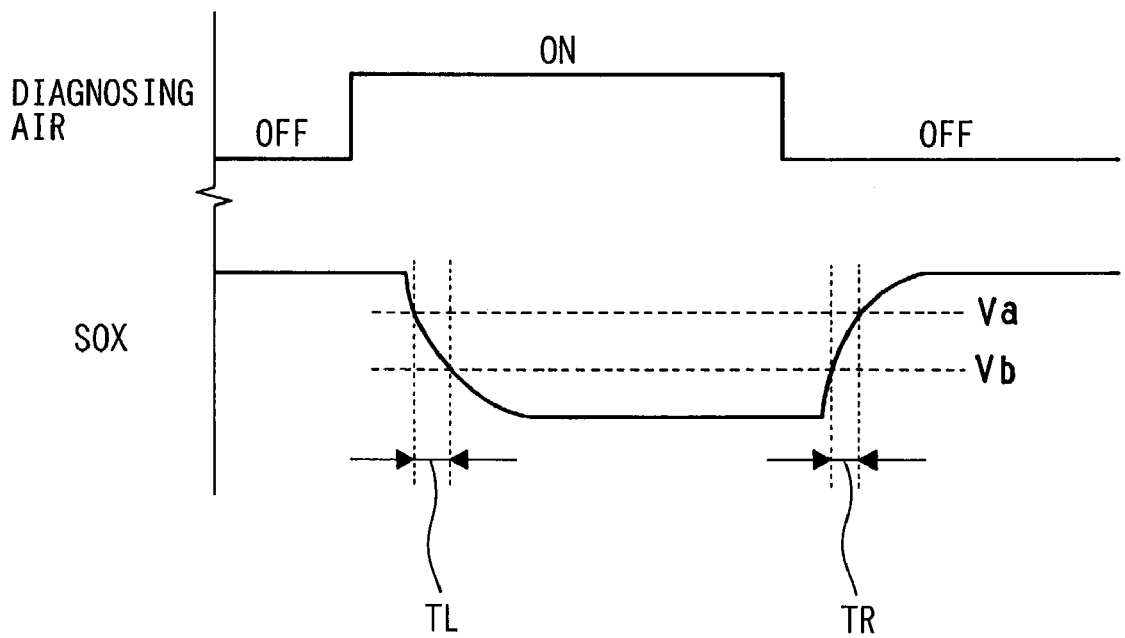
FIG. 20 is a time chart showing other method of diagnosing an abnormality of an exhaust gas sensor.

Further, according to the third embodiment, as shown in FIG. 20, when the secondary air switch valve 324 is switched from the atmosphere opening position to the abnormality diagnosing gas introducing position, a time period required for the output of the downstream gas sensor 320 to pass a predetermined section of Va through Vb may be measured as the lean response time period TL. Thereafter, when the secondary air switch valve 324 is switched from the abnormality diagnosing gas introducing position to the atmosphere opening position, a time period required for the output of the downstream gas sensor 320 to pass a predetermined section of Vb through Va may be measured as the rich response time period TR. Further, the determinant V1 (Va through Vb) for measuring the lean response time period TL and the determinant V1 (Vb through Va) for measuring the rich response time period TR may be set to voltages different from each other.

Further, a change amount of the output of the downstream gas sensor 320 when the secondary air switch valve 324 is switched from the atmosphere opening position to the abnormality diagnosing gas introducing position or a change amount of the output of the downstream gas sensor 320 when the secondary air switch valve 324 is switched from the abnormality diagnosing gas introducing position to the atmosphere opening position may be compared with a predetermined abnormality determinant and whether the lean response or the rich response of the downstream gas sensor 320 is abnormal may be determined by whether the change amount of the output of the downstream gas sensor 320 is smaller than the abnormality determinant.

Further, in this case, the abnormality determinant may be set in accordance with a change amount of the air/fuel ratio or a physical amount correlated therewith (for example, a change amount of a flow rate of the secondary air) when the secondary air switch valve 324 is switched. Thereby, a proper abnormality determinant can be set in correspondence with a change of the change amount of the output of the downstream gas sensor 320 in accordance with the change amount of the air/fuel ratio when the secondary air is switched to be introduced or stopped to introduce.

Further, when the secondary air (abnormality diagnosing gas) is directly introduced to the catalyst downstream side exhaust pipe 317b (upstream side of downstream gas sensor 320) without passing the catalyst 318, the air/fuel ratio of exhaust gas flowing at the periphery of the downstream gas sensor 320 can be changed without undergoing the influence of the catalyst 318.

According to the third embodiment, a state of introducing the secondary air into the catalyst downstream side exhaust pipe 317b is changed by the abnormality diagnosing gas introducing apparatus 327 to thereby change the air/fuel ratio of exhaust gas flowing at the periphery of the downstream gas sensor 320 into a lean direction or a rich direction (stoichiometric direction) and abnormality of the downstream gas sensor 320 is diagnosed by measuring the response time period of the downstream gas sensor 320 at that occasion. Thereby, abnormality of the downstream gas sensor 320 can be diagnosed without being influenced by the catalyst 318 and presence or absence of abnormality of the downstream gas sensor 320 can accurately be determined.

Further, abnormality diagnosis can be carried out by forcibly changing the state of introducing the secondary air by the abnormality diagnosing gas introducing apparatus 327. Therefore, it is not necessary to carry out abnormality diagnosis after awaiting for a change in the air/fuel ratio under predetermined conditions and the frequency of executing abnormality diagnosis can be ensured without being influenced by a method of operating the vehicle and road situation. When abnormality of the downstream gas sensor 320 is brought about, the abnormality can be detected at early time. Further, it is not necessary to forcibly change the air/fuel ratio on the upstream side of the catalyst 318 (target air/fuel ratio) in diagnosing abnormality. Therefore, even in executing abnormality diagnosis, an air/fuel ratio feedback control can be continued based on the output of the exhaust gas sensor 319 on the upstream side and adverse influence is not applied to running function or exhaust cleaning function of the catalyst 318. Further, in the case of the secondary air, even when the secondary air is introduced directly into the catalyst downstream side exhaust pipe 317b without passing the catalyst 318 and discharged to outside as it is, exhaust emission is not deteriorated.

Further, according to the third embodiment, by connecting the abnormality diagnosing gas introducing pipe 325 and the atmosphere opening pipe 326 to the middle of the secondary air introducing pipe 321 of the secondary air introducing apparatus 323 via the secondary air switch valve 324, the abnormality diagnosing gas introducing apparatus 327 is constructed with utilizing the secondary air introducing apparatus 323. Therefore, the cost can be reduced in comparison with a case in which all of the abnormality gas introducing apparatus 327 is constructed with exclusive parts.

However, it is not necessarily needed to construct the abnormality diagnosing gas introducing apparatus 327 by utilizing the secondary air introducing apparatus 323 but an exclusive abnormality diagnosing gas introducing apparatus for introducing outside air into the catalyst downstream side exhaust pipe 317b as abnormality diagnosing gas may be installed. Thereby, the invention is applicable to a system which is not provided with the secondary air introducing apparatus 323.

Further, according to the third embodiment, in measuring the response time period of the downstream gas sensor 320, the state of introducing the secondary air into the catalyst downstream side exhaust pipe 317b and the state of stopping to introduce the secondary air are switched. Therefore, the air/fuel ratio of exhaust gas flowing at the periphery of the downstream gas sensor 320 can significantly be changed in a comparatively short period of time and the difference of the response time period can be increased between the normal exhaust gas sensor and the abnormal exhaust gas sensor and accuracy of diagnosing abnormality of the downstream gas sensor 320 can be promoted.

Meanwhile, when the output of the downstream gas sensor 320 has already become a lean value before introducing the secondary air into the catalyst downstream side exhaust pipe 317b, even in the case in which the secondary air is introduced under the state, it is difficult that introduction of the secondary air emerges as a change in the output of the downstream gas sensor 320 and a change width of the output of the downstream gas sensor 320 is reduced. Therefore, there is a concern of deteriorating accuracy of diagnosing abnormality of the downstream gas sensor 320.

As a countermeasure against it, when the output of the downstream gas sensor 320 becomes leaner than the predetermined value before introducing the secondary air into the catalyst downstream side exhaust pipe 317b, abnormality diagnosis of the downstream side discharge gas sensor 320 may be prohibited by determining that the change width of the output of the downstream gas sensor 320 is small even when the abnormality diagnosing gas is introduced (it is difficult to accurately diagnose abnormality of the downstream gas sensor 320.) Thereby, the deterioration of the accuracy of diagnosing abnormality of the downstream gas sensor 320 can be prevented beforehand.

Further, the fuel injection amount may be corrected to increase such that the output of the downstream gas sensor 320 becomes richer than the predetermined value before introducing the secondary air. Thereby, even when the output of the downstream gas sensor 320 becomes the lean value before introducing the secondary air, the output of the downstream gas sensor 320 can be made to be richer than the predetermined value by correcting to increase the fuel injection amount before introducing the secondary air and the change width of the output of the downstream gas sensor 320 can be increased when the secondary air is introduced. Thereby, normality/abnormality of the downstream gas sensor 320 can easily be determined and accuracy of diagnosing abnormality of the downstream gas sensor 320 can be promoted.

Further, the method of diagnosing abnormality of the downstream gas sensor 320 may be changed and for example, when the response time of the downstream gas sensor 320 is measured, the air/fuel ratio of the exhaust gas flowing at the periphery of the downstream gas sensor 320 may be changed by increasing or reducing an amount of introducing the secondary air to be introduced into the catalyst downstream side exhaust pipe 317b by a predetermined amount.

(Fourth Embodiment)

Figure 21:
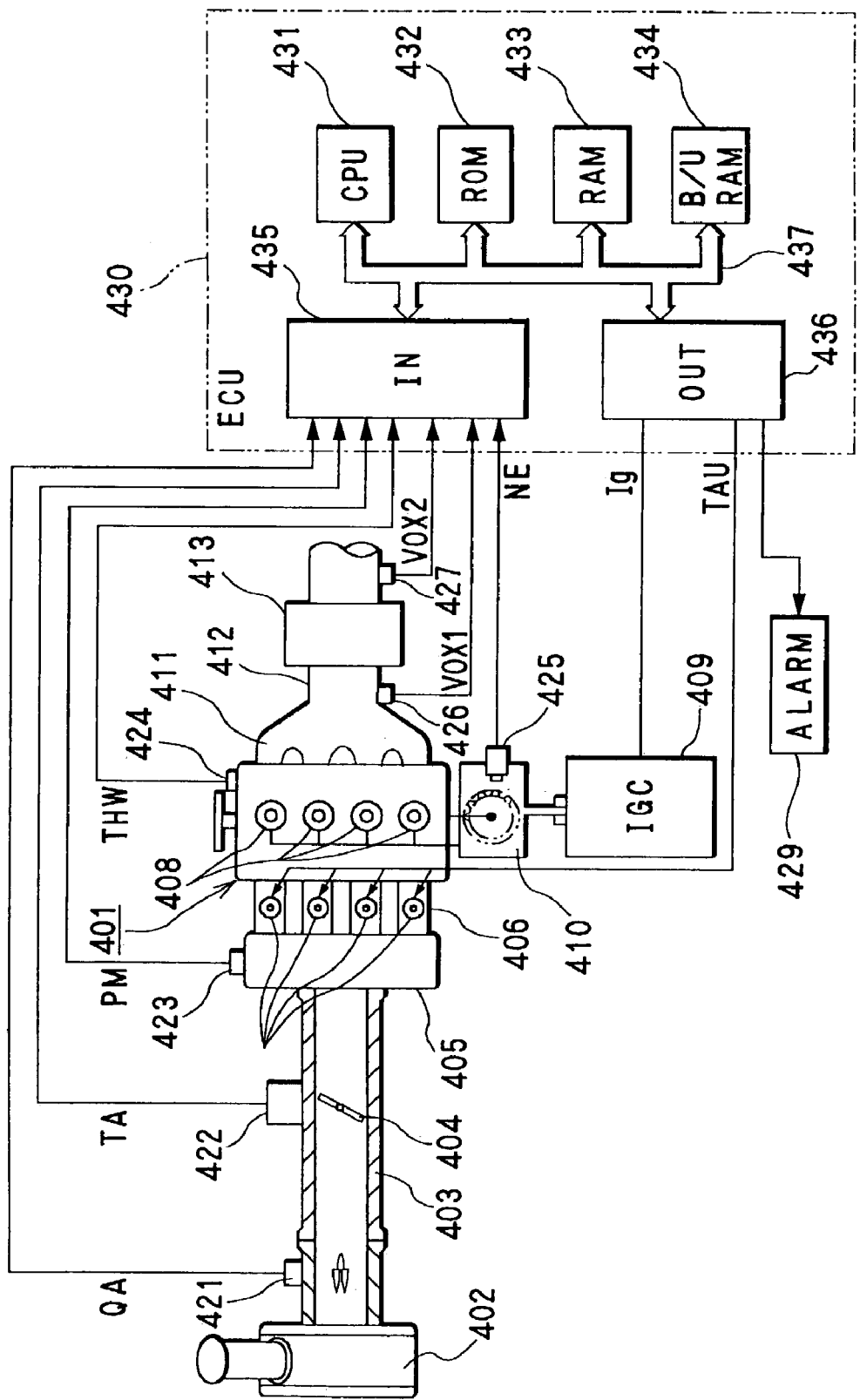
FIG. 21 is a schematic view showing an abnormality diagnosing apparatus of an exhaust gas sensor according to a fourth embodiment of the invention.

In the fourth embodiment, as shown in FIG. 21, an internal combustion engine 401 is constructed as 4-cylinder 4-cycle spark ignition type. The intake air passes an air cleaner 402, an intake path 403, a throttle valve 404, a surge tank 405 and an intake manifold 406 and mixed with fuel injected from an injector (fuel injection valve) 407 at inside of the intake manifold 406 and supplied to distribute to each cylinder as a mixture gas having a predetermined air/fuel ratio. Further, high voltage supplied from an ignition circuit (IGC) 409 is supplied to distribute to an ignition plug 408 installed at each cylinder of the internal combustion engine 401 by a distributor 410.

The mixture gas of each cylinder is combusted by spark ignition of the ignition plug 408 at predetermined time points. Further, exhaust gas after combustion passes through an exhaust manifold 411 and an exhaust path 412 and CO (carbon monoxide), HC (hydrocarbon) and NOx (nitrogen oxides) which are harmful components are cleaned by a three-way catalyst 413 provided at the exhaust path 412 and carrying a catalyst component of platinum or rhodium and an additive of cerium or Tantalum and discharged to the atmosphere.

An air flow meter 421 is provided at the intake path 403 on the downstream side of the air cleaner 402 and an intake amount QA per unit time passing the air cleaner 402 is detected by the air flow meter 421. Further, the throttle valve 404 is provided with a throttle opening degree sensor 422. An analog signal in accordance with a throttle opening degree TA is detected by the throttle opening degree sensor 422 and it is detected that the throttle valve 404 is substantially fully closed by an ON/OFF signal from an idle switch, not illustrated. Further, the surge tank 405 is provided with an intake pressure sensor 423 and intake pressure PM is detected by the intake pressure sensor 423. Further, a water temperature sensor 424 is provided on a cylinder block of the internal combustion engine 401 and cooling water temperature THW of the internal combustion engine 401 is detected by the water temperature sensor 424.

The distributor 410 is provided with a rotational angle sensor 425 for detecting engine rotational speed NE of the internal combustion engine 401 and pulse signals are outputted from the rotational angle sensor 425 by 24 times for 2 rotations of a crankshaft (not illustrated) of the internal combustion engine 401, that is, at each 720 (° CA (crank angle)). Further, on the upstream side of the three-way catalyst 413 of the exhaust path 412, an A/F sensor 426 for outputting a linear air/fuel ratio signal VOX1 in accordance with an air/fuel ratio λ of exhaust gas exhausted from the internal combustion engine 401. On the downstream side of the three-way catalyst 413, an oxygen ($O_2$) sensor 427 for outputting a voltage signal VOX2 in accordance with the air/fuel ratio λ of exhaust gas is rich or lean relative to the stoichiometric air/fuel ratio (λ=1) is provided.

ECU 430 for controlling an operating state of the internal combustion engine 401 comprises a logic operation circuit centering on CPU 431 as a central processing unit for executing well-known various operation processing, ROM 432 storing control programs and control maps, RAM 433 storing various data and B/U (backup) RAM 434 and connected to an input port 435 for inputting detected signals from the various sensors and an output port 436 for outputting control signals to various actuators via a bus 437.

Further, ECU 430 is inputted with the intake amount QA, the intake pressure PM, the throttle opening degree TA, the cooling water temperature THW, the engine rotational speed NE, the air/fuel ratio signal VOX1 and the voltage signal VOX2 from the various sensors via the input port 435, a fuel injection amount TAU and an ignition time point Ig are calculated based on the respective values. The control signals are respectively outputted to the injector 407 and the ignition circuit 409 via the output port 436. Further, in ECU 430, the sensor characteristic abnormality detecting processing is executed, presence or absence of occurrence of abnormality of the oxygen sensor 427 is diagnosed. If abnormality is determined, an alarm light 429 is lighted by a signal outputted via the output port 436 and the occurrence of abnormality is alarmed to a driver.

The processing procedure of calculating a target air/fuel ratio λTG in CPU 431 will be described based on a flow chart of FIG. 22 in reference to FIG. 23. Here, FIG. 23 is a map for setting a base target air/fuel ratio λTGBSE in FIG. 22 with the intake amount QA (g/sec). Further, the target air/fuel ratio calculation routine is repeatedly executed by CPU 431 at each predetermined time period.

Figure 22:
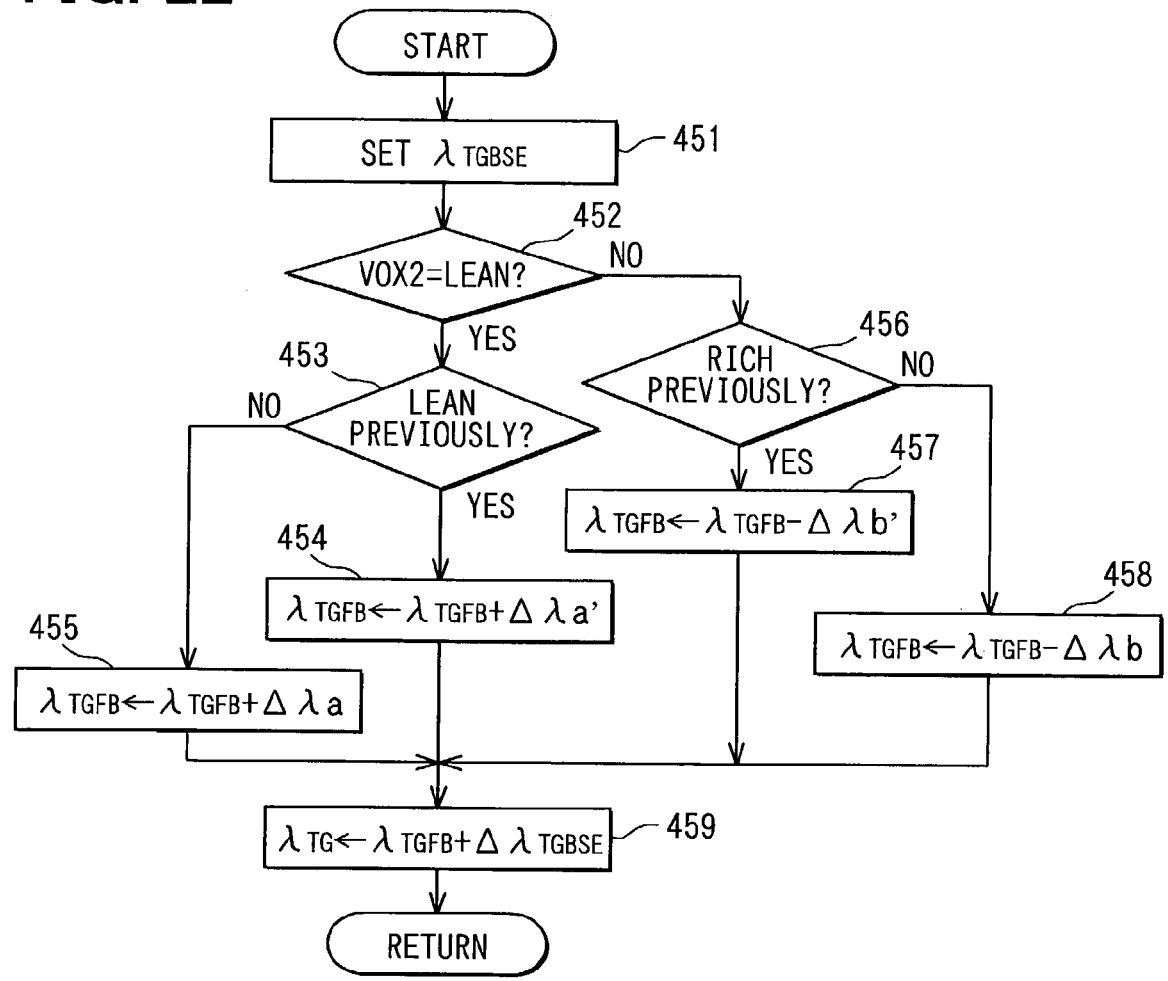
FIG. 22 is a flowchart showing a processing procedure of calculating a target air/fuel ratio in the abnormality diagnosing apparatus of the exhaust gas sensor according to the fourth embodiment.
Figure 23:
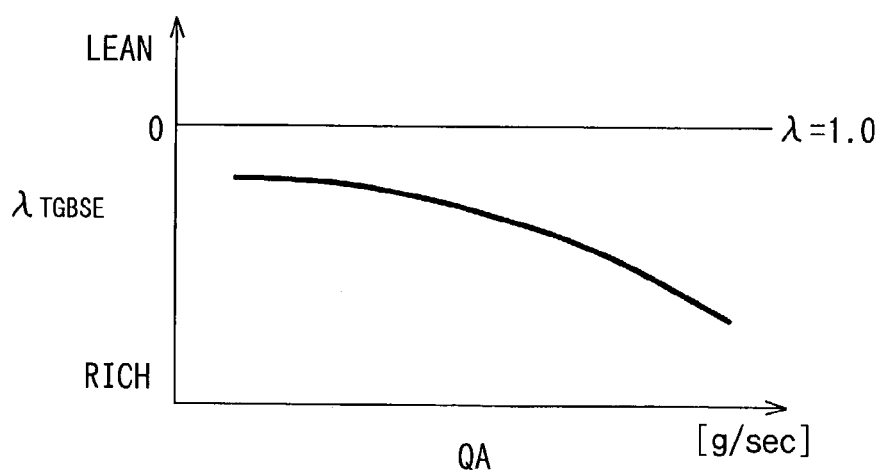
FIG. 23 is a map for setting a base target air/fuel ratio by taking an intake air amount as a parameter.

In FIG. 22, at step 451, the base target air/fuel ratio λTGBSE with respect to the current intake amount QA is set by the map of FIG. 23. As the base target air/fuel ratio λTGBSE, a target air/fuel ratio λTG requested at the three-way catalyst 413 is previously given in a feed forward manner. Further, as shown by the map of FIG. 23, the more increased is the intake amount QA, to the richer side of the base target air/fuel ratio λTGBSE the output of the oxygen sensor 27 is set to control to a predetermined value.

By adding the setting, center of a target air/fuel ratio F/B correction amount λTGFB in an air/fuel ratio F/B (feedback) control can be controlled to a vicinity of "0 (null)" regardless of the operating condition. However, as other factors, for example, there is a case in which the target air/fuel ratio F/B correction amount λTGFB is deviated by influence of a difference in the A/F sensor 426 on the upstream side of the three-way catalyst 413, also in this case, the correction amount is changed centering on the predetermined value and a change thereof by the operating condition can be reduced.

Next, the processing proceeds to step 452 to determine whether the output VOX2 from the oxygen sensor 427 on the downstream side of the three-way catalyst 413 is lean. When the determining condition at step 452 is established, that is, when the output VOX2 from the oxygen sensor 427 is lean, the processing proceeds to step 453 to determine whether the output is lean also at a previous time. When the determining condition at step 453 is established, that is, when the output from the oxygen sensor 427 is lean at previous time and at current time, the processing proceeds to step 454 and the target air/fuel ratio F/B correction amount λTGFB at previous time is added with a predetermined amount Δλa' to update the target air/fuel ratio F/B correction amount λTGFB.

Meanwhile, when the determining condition at step 453 is not established, that is, when the output is rich at previous time and the output becomes lean for the first time at current time, the processing proceeds to step 455 and a predetermined amount Δλa is added to the target air/fuel ratio F/B correction amount λTGFB at previous time to update the target air/fuel ratio F/B correction amount λTGFB.

Meanwhile, when the determining condition at step 452 is not established, that is, when the output from the oxygen sensor 427 is rich, the processing proceeds to step 456 to determine whether the output is rich also at previous time. When the determining condition at step 456 is established, that is, when the output from the oxygen sensor 427 is rich both at previous time and current time, the processing proceeds to step 457 and a predetermined amount ΔλB' is subtracted from the target air/fuel ratio F/B correction amount λTGFB at previous time to update the target air/fuel ratio F/B correction amount λTGFB.

Meanwhile, when the determining condition at step 456 is not established, that is, when the output is lean at previous time and becomes rich for the first time at current time, the processing proceeds to step 458 and a predetermined amount ΔλB is subtracted from the target air/fuel ratio F/B correction amount λTGFB at previous time to update the target air/fuel ratio F/B correction amount λTGFB. After calculating the target air/fuel ratio F/B correction amount λTGFB by the processing at step 454, step 455, step 457 or step 458, the processing proceeds to step 459 and the target air/fuel ratio λTG is calculated by adding the target air/fuel ratio F/B correction amount λTGFB to the base target air/fuel ratio λTGBSE set at step 451 and the routine is finished.

Figure 24:
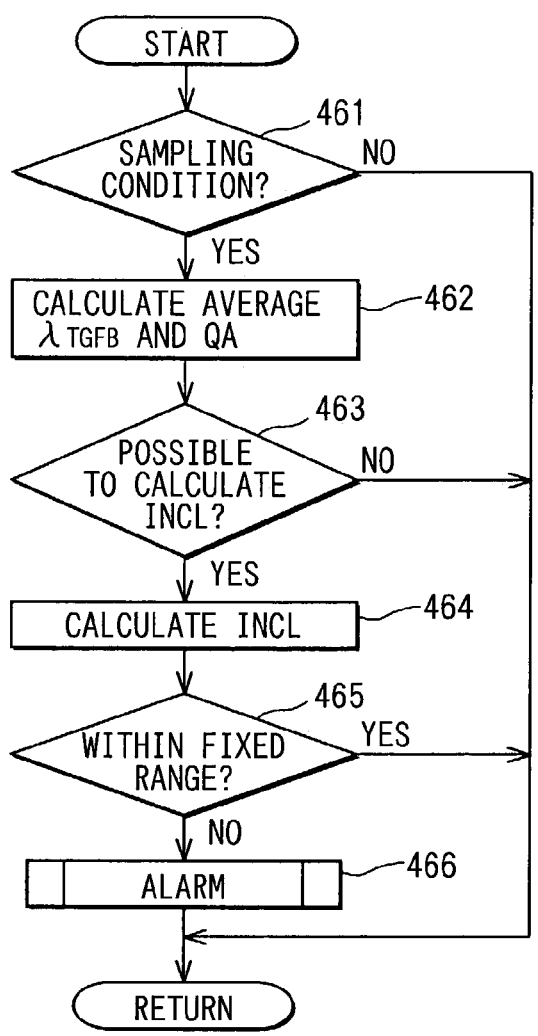
FIG. 24 is a flowchart showing a processing procedure of a sensor property abnormality diagnosis of an exhaust gas sensor.
Figure 25:
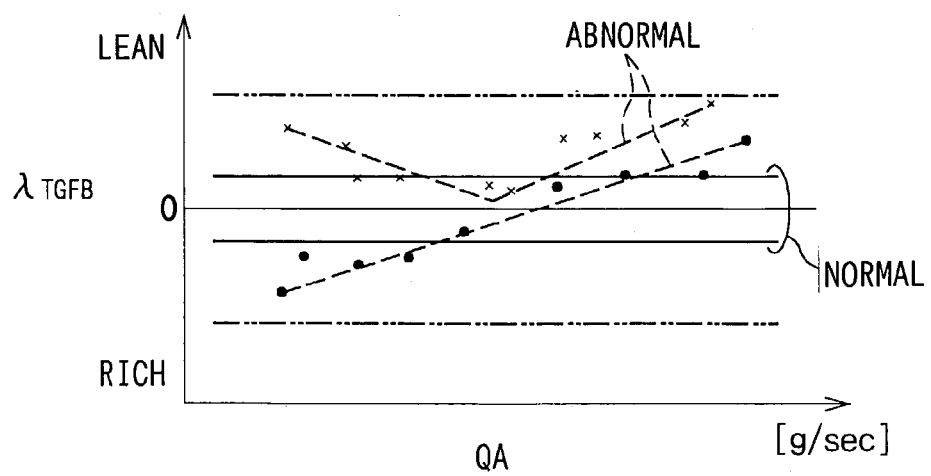
FIG. 25 is a characteristic diagram showing a relationship between an intake air amount and a target air/fuel ratio F/B correction amount.

Next, the processing of a sensor characteristic abnormality diagnosis of the exhaust gas sensor 427 is described based on a flowchart of FIG. 24 in reference to FIG. 25. Here, FIG. 25 is a characteristic graph showing a relationship between the intake amount QA (g/sec) as the operating condition of the internal combustion engine 401 and the target air/fuel ratio F/B correction amount λTGFB used in FIG. 24. The normal state of the oxygen sensor 427 is indicated by bold lines, and the abnormal state is indicated by broken lines. A case, in which the characteristic is shifted by other factor although the oxygen sensor 427 is normal, is shown by a two-dotted chain line. Further, the sensor characteristic abnormality detecting routine is repeatedly executed by CPU 431 at each predetermined time period.

In FIG. 24, first, at step 461, it is determined whether a sampling condition is established. As establishment of the sampling condition, for example, there are pointed out that the A/F sensor 426 on the upstream side of the three-way catalyst 413 is normal, that main air/fuel ratio F/B control by the A/F sensor 426 is being carried out and sub-air/fuel ratio F/B by the oxygen sensor 427 is being carried out, and that the output of the oxygen sensor 427 falls in a predetermined range.

When the determining condition at step 461 is established, that is, when the sampling condition is established, the processing proceeds to step 462, and the target air/fuel ratio F/B correction amount λTGFB calculated and averaged in FIG. 22 and the averaged intake amount QA at that occasion are respectively calculated. Next, the processing proceeds to step 463 and it is determined whether the inclination INCL of the target air/fuel ratio F/B correction amount λTGFB can be calculated. In this case, whether the inclination INCL of the target air/fuel ratio F/B correction amount λTGFB can be calculated is determined when a sampling number is equal to or larger than a predetermined value or when upper and lower limit values of the intake amount QA in sampling are remote from each other by a predetermined value or more at step 462.

When the determining condition at step 463 is established, the processing proceeds to step 464 and the inclination INCL (rate of λTGFB to QA, that is, λTGFB/QA) of the target air/fuel ratio F/B correction amount λTGFB is calculated. Next, the processing proceeds to step 465 to determine whether the inclination INCL of the target air/fuel ratio F/B correction amount λTGFB calculated at step 464 falls in a predetermined fixed range. When the determining condition at step 465 is not established, that is, when the inclination of the target air/fuel ratio F/B correction amount λTGFB is calculated as shown by the broken line in FIG. 25 and does not fall in the predetermined range when the oxygen sensor 427 is normal indicated by the bold line in FIG. 25, the processing proceeds to step 466, the alarm light 429 is lighted and occurrence of abnormality is alarmed to the driver as an alarming processing when the oxygen sensor 427 is abnormal. At the same time, a well-known diagnosis processing is executed and the routine is finished.

Meanwhile, when the determining condition at step 461 is not established, that is, when the sampling condition is not established, or when the determining condition at step 463 is not established, that is, when the inclination INCL of the target air/fuel ratio F/B correction amount λTGFB cannot be calculated or when the determining condition at step 465 is established, that is, when the inclination INCL of the target air/fuel ratio F/B correction amount λTGFB is calculated as shown by the bold lines in FIG. 25 to fall in a predetermined range when the oxygen sensor 427 is normal, the routine is finished.

Next, a modified example of the fourth embodiment will be described based on a flowchart of FIG. 26 in reference to FIG. 27. Here, FIG. 27 is a distribution diagram showing the frequency F of the target air/fuel ratio F/B correction amount λTGFB with respect to the intake amount QA (g/sec) as the operating condition of the internal combustion engine 401 used in FIG. 26, the normal state of the oxygen sensor 427 is designated by a bold line, the abnormal state is indicated by a broken line. The case, in which the correction amount is shifted by other factor although the oxygen sensor 427 is normal, is indicated by two-dotted chain lines. Further, the sensor characteristic abnormality detecting routine is repeatedly executed by CPU 431 at each predetermined time period.

Figure 26:
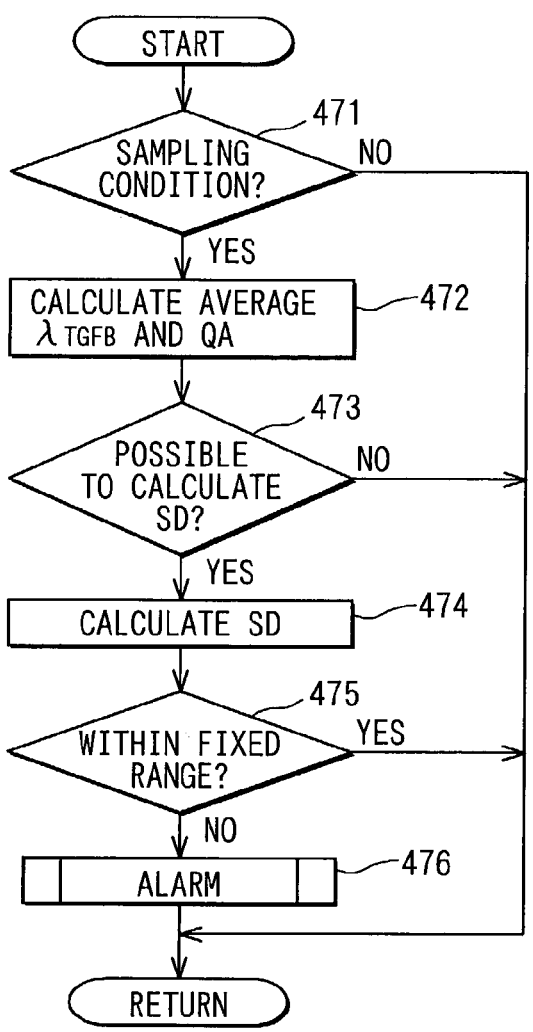
FIG. 26 is a flowchart showing a modified example of a processing procedure of sensor property abnormality diagnosis of an exhaust gas sensor.
Figure 27:
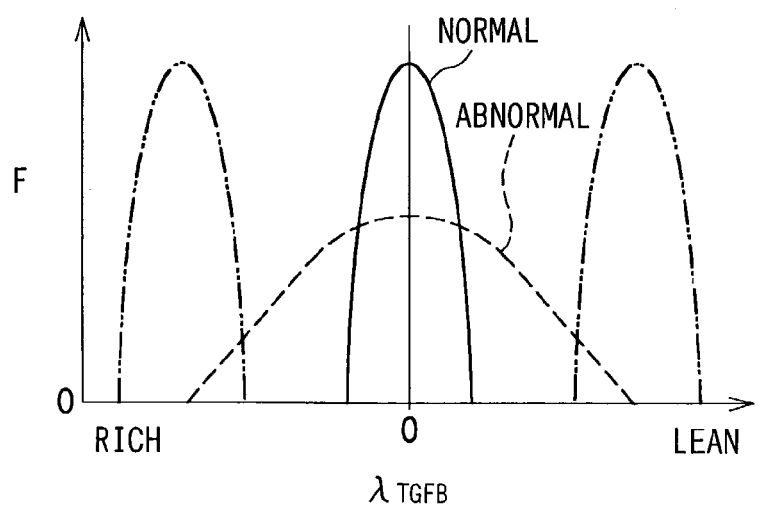
FIG. 27 is a distribution diagram showing the frequency of a target air/fuel ratio feedback correction amount with respect to an intake air amount in a modified example of FIG. 26.

In FIG. 26, first, at step 471, similar to the above embodiment, it is determined whether the sampling condition is established. When the determining condition at step 471 is established, that is, when the sampling condition is established, the processing proceeds to step 472 and the target air/fuel ratio F/B correction amount λTGFB calculated and averaged in FIG. 22 and the averaged intake amount QA at that occasion are calculated. Next, the processing proceeds to step 473 and it is determined whether the standard deviation SD of the target air/fuel ratio F/B correction amount λTGFB can be calculated.

When the determining condition at step 473 is established, when processing proceeds to step 474 and the standard deviation SD of the target air/fuel ratio F/B correction amount λTGFB is calculated. Next, the processing proceeds to step 475 and it is determined whether the calculated standard deviation SD of the target air/fuel ratio F/B correction amount λTGFB falls in a fixed range. When the determining condition at step 475 is not established, that is, when the standard deviation SD of the target air/fuel ratio F/B correction amount λTGFB is calculated as shown by the broken line and does not fall in the predetermined range when the oxygen sensor 427 is normal indicated by the bold line in FIG. 27, the processing proceeds to step 476, the alarm light 429 is lighted and occurrence of abnormality is alarmed to the driver as the alarming processing when the oxygen sensor 427 is abnormal. At the same time, a well-known diagnosis processing is executed and the routine is finished.

Meanwhile, when the determining condition at step 471 is not established, that is, when the sampling condition is not established, or when the determining condition at step 473 is not established, that is, when the standard deviation SD of the target air/fuel ratio F/B correction amount λTGFB cannot be calculated, or when the determining condition at step 475 is established, that is, when the standard deviation of the target air/fuel ratio F/B correction amount λTGFB is calculated as shown by the bold line in FIG. 27 and falls in the predetermined range when the oxygen sensor 427 is normal, the routine is finished without processing further.

The above embodiments and modifications may be altered further without departing from the spirit of the invention.

What is claimed is:

1. An abnormality diagnosing apparatus of an exhaust gas sensor comprising:
   an exhaust gas sensor installed in an exhaust gas path of an internal combustion engine; and
   sensor abnormality diagnosing means for diagnosing presence or absence of an abnormality of the exhaust gas sensor based on an output of the exhaust gas sensor produced after stopping the internal combustion engine.

2. The abnormality diagnosing apparatus of an exhaust gas sensor according to claim 1,
   wherein the sensor abnormality diagnosing means executes an abnormality diagnosis of the exhaust gas sensor based on a change in the output of the exhaust gas sensor produced by flowing atmospheric air back into the exhaust gas path after stopping the internal combustion engine.

3. The abnormality diagnosing apparatus of an exhaust gas sensor according to claim 1,
   wherein the exhaust gas sensor is installed downstream a catalyst for cleaning exhaust gas of the internal combustion engine.

4. The abnormality diagnosing apparatus of an exhaust gas sensor according to claim 1, further comprising:
   fuel correcting means for correcting fuel amount for the internal combustion engine immediately before stopping the internal combustion engine.

5. The abnormality diagnosing means of an exhaust gas sensor according to claim 1, further comprising:
   abnormality diagnosis prohibiting means for prohibiting abnormality diagnosis of the exhaust gas sensor when the output of the exhaust gas sensor in stopping the internal combustion engine is leaner than a predetermined value.

6. The abnormality diagnosing apparatus of an exhaust gas sensor according to claim 1,
   wherein the sensor abnormality diagnosing means sets a determining condition of diagnosing the abnormality of the exhaust gas sensor in accordance with the output of the exhaust gas sensor in stopping the internal combustion engine.

7. An abnormality diagnosing apparatus of an exhaust gas sensor comprising:
   a downstream exhaust gas sensor installed on a downstream side of a catalyst in an exhaust gas path of an internal combustion engine; and
   sensor abnormality diagnosing means for diagnosing presence or absence of an abnormality of the downstream exhaust gas sensor based on an output of the downstream gas sensor,
   wherein the sensor abnormality diagnosing means executes an abnormality diagnosis of the downstream gas sensor based on the output of the downstream gas sensor in an operating region exceeding a cleaning function of the catalyst, in which exhaust gas of the internal combustion engine passes through the catalyst without being cleaned.

8. The abnormality diagnosing apparatus of an exhaust gas sensor according to claim 7,
   wherein the sensor abnormality diagnosing means executes the abnormality diagnosis of the downstream gas sensor by changing an air/fuel ratio of an upstream side of the catalyst when an intake air amount of the internal combustion engine is increased to the region of exceeding the cleaning function of the catalyst.

9. The abnormality diagnosing apparatus of an exhaust gas sensor according to claim 8,
   wherein the sensor abnormality diagnosing means sets a range of the intake air amount for executing the abnormality diagnosis of the downstream gas sensor in accordance with a degree of deterioration of the catalyst.

10. The abnormality diagnosing apparatus of an exhaust gas sensor according to claim 7,
    wherein the sensor abnormality diagnosing means executes the abnormality diagnosis of the downstream gas sensor by changing an air/fuel ratio when the air/fuel ratio at an upstream side of the catalyst falls in a region of exceeding the cleaning function of the catalyst.

11. An abnormality diagnosing apparatus of an exhaust gas sensor comprising:
    a downstream gas sensor installed on a downstream side of a catalyst for cleaning an exhaust gas of an internal combustion engine;
    abnormality diagnosing means for diagnosing presence or absence of an abnormality of the downstream gas sensor based on an output of the downstream gas sensor; and
    diagnosing gas introducing means for introducing an abnormality diagnosing gas to an upstream side of the downstream gas sensor in an exhaust path at the downstream side of the catalyst when the presence or absence of an abnormality is to be diagnosed,
    wherein the abnormality diagnosing means executes an abnormality diagnosis of the downstream gas sensor by introducing the abnormality diagnosing gas to the upstream side of the downstream gas sensor by the diagnosing gas introducing means when the abnormality diagnosis is to be attained.

12. The abnormality diagnosing apparatus of an exhaust gas sensor according to claim 11,
    wherein the diagnosing gas introducing means introduces air to the upstream side of the downstream gas sensor as the abnormality diagnosing gas.

13. The abnormality diagnosing apparatus of an exhaust gas sensor according to claim 12, further comprising:
    secondary air introducing means for introducing secondary air into the exhaust path at the upstream side of the catalyst;
    wherein the diagnosing gas introducing means introduces the secondary air supplied from the secondary air introducing means to the upstream side of the downstream gas sensor as the abnormality diagnosing gas.

14. The abnormality diagnosing apparatus of an exhaust gas sensor according to claim 11,
    wherein the sensor abnormality determining means executes the abnormality diagnosis of the downstream gas sensor based on a change in the output of the downstream gas sensor produced by switching a state of introducing the abnormality diagnosing gas to the upstream side of the downstream gas sensor and a state of stopping to introduce the abnormality diagnosing gas.

15. The abnormality diagnosing apparatus of an exhaust gas sensor according to claim 14, further comprising:
    abnormality diagnosis prohibiting means for prohibiting the abnormality diagnosis by the sensor abnormality diagnosing means when the output of the downstream gas sensor is leaner than a predetermined value before introducing the abnormality diagnosing gas to the upstream side of the downstream gas sensor.

16. The abnormality diagnosing apparatus of an exhaust gas sensor according to claim 14, further, comprising:
rich controlling means for controlling a fuel amount for the engine such that the output of the downstream gas sensor becomes richer than a predetermined value before introducing the abnormality diagnosing gas to the upstream side of the downstream gas sensor.

17. The abnormality diagnosing apparatus of an exhaust gas sensor according to claim 14,
wherein the sensor abnormality diagnosing means determines the abnormality of the downstream gas sensor when an amount of changing the output of the downstream gas sensor is smaller than a predetermined abnormality determinant in switching a state of introducing the abnormality diagnosing gas to the upstream side of the downstream gas sensor and a state of stopping to introduce the abnormality diagnosing gas.

18. The abnormality diagnosing apparatus of an exhaust gas sensor according to claim 17,
wherein the sensor abnormality diagnosing means sets the abnormality determinant in accordance with an amount of changing an air/fuel ratio or a physical amount correlated therewith in switching the state of introducing the abnormality diagnosing gas to the upstream side of the downstream gas sensor and the state of stopping to introduce the abnormality diagnosing gas.

19. An abnormality detecting apparatus of an exhaust gas sensor comprising:
a catalyst arranged in an exhaust path of an internal combustion engine for cleaning exhaust gas of the internal combustion engine;
an exhaust gas sensor arranged downstream the catalyst for detecting an oxygen concentration of the exhaust gas from the catalyst;
correction amount setting means for setting a plurality of correction amounts for correcting an air/fuel ratio of mixture of the internal combustion engine based on respective detected values of the exhaust gas sensor for respective operating conditions of the internal combustion engine;
storing means for storing the correction amounts set by the correction amount setting means; and
abnormality detecting means for detecting an abnormality of the exhaust gas sensor based on the plurality of correction amounts stored in the storing means for respective operating conditions of the internal combustion engine.

20. The abnormality detecting apparatus of an exhaust gas sensor according to claim 19,
wherein the respective operating conditions are defined by an intake air amount of the internal combustion engine, and
wherein the abnormality detecting means detects the abnormality of the exhaust gas sensor based on an inclination of the correction amounts relative to the intake air amount.

21. The abnormality detecting apparatus of an exhaust gas sensor according to claim 19,
wherein the respective operating conditions are defined by an intake air amount of the internal combustion engine, and
wherein the abnormality detecting means detects the abnormality of the exhaust gas sensor based on a distribution of the correction amounts with respect to the intake air amount.

22. The abnormality detecting apparatus of an exhaust gas sensor according to claim 20,
wherein the abnormality detecting means determines the abnormality of the exhaust gas sensor when the inclination of at least one of the correction amounts relative to the intake air amount exceeds a fixed range of the inclination.

23. The abnormality detecting apparatus of an exhaust gas sensor according to claim 21,
wherein the abnormality detecting means determines the abnormality of the exhaust gas sensor when the distribution of at least one of the correction amounts relative to the intake air amount exceeds a fixed range of the distribution.

24. A method of diagnosing an abnormality of an exhaust gas sensor, the method comprising:
installing an exhaust gas sensor in an exhaust gas path of an internal combustion engine; and
diagnosing presence or absence of an abnormality of the exhaust gas sensor based on an output of the exhaust gas sensor produced after stopping the internal combustion engine.

25. The method as in claim 24 wherein the abnormality diagnosis of the exhaust gas sensor is executed based on a change in the output of the exhaust gas sensor produced by flowing atmospheric air back into the exhaust gas path after stopping the internal combustion engine.

26. A method of diagnosing an abnormality of an exhaust gas sensor, the method comprising:
installing a downstream exhaust gas sensor on a downstream side of a catalyst in an exhaust gas path of an internal combustion engine; and
diagnosing presence or absence of an abnormality of the downstream exhaust gas sensor based on an output of the downstream gas sensor,
wherein the abnormality diagnosis of the downstream gas sensor is executed based on the output of the downstream gas sensor in an operating region exceeding a cleaning function of the catalyst, in which exhaust gas of the internal combustion engine passes through the catalyst without being cleaned.

27. The method as in claim 26 wherein the abnormality diagnosis of the downstream gas sensor is executed by changing an air/fuel ratio of an upstream side of the catalyst when an intake air amount of the internal combustion engine is increased to the region of exceeding the cleaning function of the catalyst.

28. The method as in claim 27 wherein a range of the intake air amount is set for executing the abnormality diagnosis of the downstream gas sensor in accordance with a degree of deterioration of the catalyst.

29. The method as in claim 26 wherein the abnormality diagnosis of the downstream gas sensor is executed by changing an air/fuel ratio when the air/fuel ratio at an upstream side of the catalyst falls in a region of exceeding the cleaning function of the catalyst.

30. A method of diagnosing an abnormality of an exhaust gas sensor, the method comprising:
installing a downstream gas sensor on a downstream side of a catalyst for cleaning an exhaust gas of an internal combustion engine;
diagnosing presence or absence of an abnormality of the downstream gas sensor based on an output of the downstream gas sensor; and
introducing an abnormality diagnosing gas to an upstream side of the downstream gas sensor in an exhaust path at the downstream side of the catalyst when the presence or absence of an abnormality is to be diagnosed, wherein the abnormality diagnosis of the downstream gas sensor is executed by introducing the abnormality diagnosing gas to the upstream side of the downstream gas sensor when the abnormality diagnosis is to be attained.

31. The method as in claim 30 wherein air is introduced to the upstream side of the downstream gas sensor as the abnormality diagnosing gas.

32. The method as in claim 30 wherein the abnormality diagnosis of the downstream gas sensor is executed based on a change in the output of the downstream gas sensor produced by switching a state of introducing the abnormality diagnosing gas to the upstream side of the downstream gas sensor and a state of stopping to introduce the abnormality diagnosing gas.

33. A method of detecting an abnormality of an exhaust gas sensor, the method comprising:

arranging a catalyst in an exhaust path of an internal combustion engine for cleaning exhaust gas of the internal combustion engine;

arranging an exhaust gas sensor downstream the catalyst for detecting an oxygen concentration of the exhaust gas from the catalyst;

setting a plurality of correction amounts for correcting an air/fuel ratio of mixture of the internal combustion engine based on respective detected values of the exhaust gas sensor for respective operating conditions of the internal combustion engine;

storing the set correction amounts; and detecting an abnormality of the exhaust gas sensor based on the plurality of stored correction amounts for respective operating conditions of the internal combustion engine.

34. The method as in claim 33 wherein the operating conditions are defined by an intake air amount of the internal combustion engine, and wherein the abnormality of the exhaust gas sensor is detected based on an inclination of the correction amounts relative to the intake air amount.

35. The method as in claim 33 wherein the operating conditions are defined by an intake air amount of the internal combustion engine, and wherein the abnormality of the exhaust gas sensor is detected based on a distribution of the correction amounts with respect to the intake air amount.

* * * * *